United States Patent
Ohuchi et al.

(10) Patent No.: US 8,224,049 B2
(45) Date of Patent: Jul. 17, 2012

(54) ULTRASONIC IMAGE PROCESSING APPARATUS AND A METHOD FOR PROCESSING AN ULTRASONIC IMAGE

(75) Inventors: Hiroyuki Ohuchi, Nasushiobara (JP); Tetsuya Kawagishi, Nasushiobara (JP); Yasuhiko Abe, Otawara (JP); Masahide Nishiura, Machida (JP); Tomoyuki Takeguchi, Kawasaki (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 909 days.

(21) Appl. No.: 12/193,315

(22) Filed: Aug. 18, 2008

(65) Prior Publication Data
US 2009/0060306 A1 Mar. 5, 2009

(30) Foreign Application Priority Data
Sep. 4, 2007 (JP) ................................. 2007-228730

(51) Int. Cl.
*G06K 9/00* (2006.01)
(52) U.S. Cl. ....................................................... 382/128
(58) Field of Classification Search ........... 382/100–150
See application file for complete search history.

(56) References Cited

U.S. PATENT DOCUMENTS

| | | | |
|---|---|---|---|
| 5,797,844 A * | 8/1998 | Yoshioka et al. | 600/442 |
| 6,859,548 B2 * | 2/2005 | Yoshioka et al. | 382/128 |
| 7,460,698 B2 * | 12/2008 | Yoshioka et al. | 382/128 |
| 2006/0291705 A1 | 12/2006 | Baumann et al. | |

FOREIGN PATENT DOCUMENTS
EP 1 722 333 A1 11/2006

OTHER PUBLICATIONS
U.S. Appl. No. 12/109,805, filed Apr. 25, 2008, Yasuhiko Abe, et al.

* cited by examiner

*Primary Examiner* — Dixomara Vargas
(74) *Attorney, Agent, or Firm* — Oblon, Spivak, McClelland, Maier & Neustadt, L.L.P.

(57) ABSTRACT

A contour specifying part receives volume data representing a subject acquired by transmission of ultrasonic waves to the subject, and specifies a 3-dimensional contour of a myocardium based on the volume data. A forming part sets a reference point on the contour of the myocardium, and forms an image generation plane including a plane substantially orthogonal to the contour of the myocardium at the reference point. An image generator generates image data on the image generation plane based on the volume data. A display controller controls a display to display an image based on the image data.

20 Claims, 11 Drawing Sheets

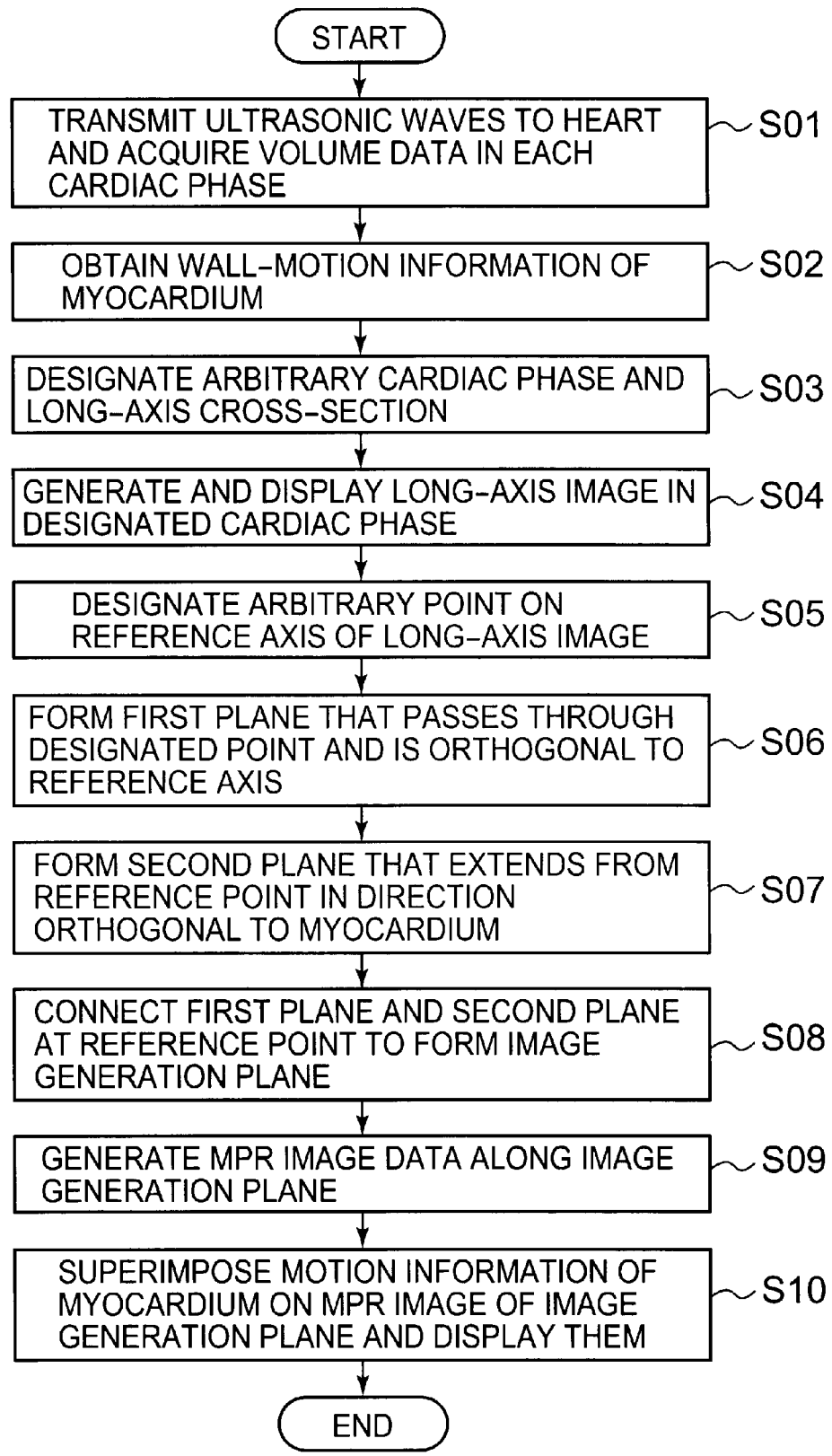

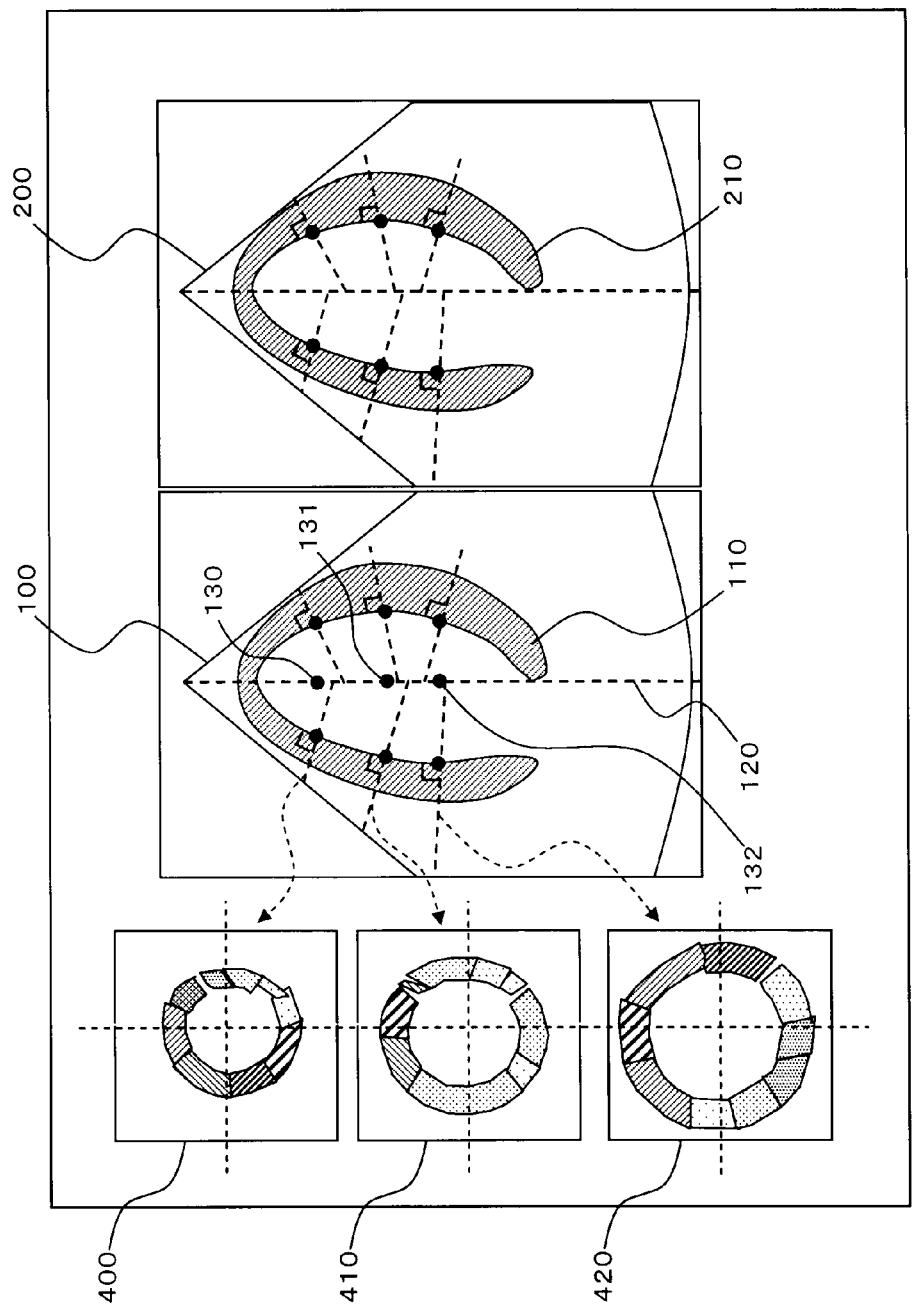

ULTRASONIC IMAGE PROCESSING APPARATUS AND A METHOD FOR PROCESSING AN ULTRASONIC IMAGE

BACKGROUND OF THE INVENTION

1. Field of the Invention

The present invention relates to an ultrasonic image processing apparatus that obtains the motion state of a subject by using an ultrasonic image of the subject acquired with ultrasonic waves, and also relates to a method for processing an ultrasonic image.

2. Description of the Related Art

Objective and quantitative evaluation of functions of body tissues such as the myocardium of a heart is very important for diagnosis of the body tissues. For example, a method of acquiring image data of a heart with an ultrasonic imaging apparatus and quantitatively evaluating based on the image data has been proposed.

For example, a method of executing a pattern matching process on images and obtaining motion information such as displacement and strain of tissues has been proposed. As a specific example, for evaluation of the myocardium of a heart, ultrasonic waves are transmitted to the heart, and volume data that represents the heart is acquired in each cardiac phase. Then, the pattern matching process is executed on the volume data, whereby the position of a local site of the myocardium is obtained in each cardiac phase and the motion of the myocardium is tracked. Based on the result of the tracking, wall motion information such as the motion vector of the myocardium and strain of the myocardium can be obtained. Then, on an MPR image generated from the volume data of the heart, the wall motion information is superimposed and displayed. In conventional techniques, a short-axis image in a short-axis cross-section of a heart is generated, and a color corresponding to the magnitude of wall motion information is assigned onto the short-axis image and displayed thereon. For example, on the short-axis image, motion information in the wall-thickness direction of the myocardium is superimposed and displayed.

Further, in the conventional techniques, a central axis is set for the myocardium represented in the volume data, a desired point is designated on the central axis by an operator, a plane is set from the designated point toward the myocardium, and an image with the plane expanded is generated and displayed (US Serial No. 2006/0291705). By this method, a plane that intersects the myocardium is set and, by generating an image on the plane, an image that represents the cross-section of the myocardium is generated.

However, the short-axis image according to the conventional technique is an image on a plane that obliquely intersects the myocardium. Thus, the short-axis image represents not the actual morphology of the myocardium but a tissue on the plane that obliquely intersects the myocardium. To be specific, a heart is a 3-dimensional object with curvatures changing spatially, so that when an arbitrary plane intersecting the heart is set, the plane is set obliquely with respect to the wall-thickness direction of the myocardium. Therefore, the short-axis image on the arbitrary plane represents the tissue on the plane set obliquely with respect to the wall-thickness direction of the myocardium.

Thus, the thickness direction of the myocardium represented in the short-axis image of the conventional technique does not necessarily coincide with the direction of a vector in the actual wall-thickness direction of the myocardium, and the thickness of the myocardium represented in the short-axis image is represented larger than the actual wall thickness. Wall motion information is motion information in the actual wall-thickness direction obtained from the volume data.

Therefore, when the wall motion information is superimposed and displayed on the myocardium represented in the short-axis image according to the conventional technique, a problem arises in which the thickness direction of the myocardium represented in the short-axis image does not coincide with the direction of the vector in the actual wall-thickness direction of the myocardium. As a result, the short-axis image with the wall motion information superimposed does not represent the actual wall motion information of the myocardium represented in the short-axis image. Therefore, in the conventional technique, it is difficult to properly evaluate a wall motion at each part of the myocardium, even if observing the morphology and wall motion information of the myocardium represented in the short-axis image.

Further, according to the method of setting a plane from the central axis toward the myocardium, there is a problem that, depending on the angle of the plane set from the central axis toward the myocardium, the shape of the cardiac cavity represented in an image on the plane significantly differs from the actual shape. For example, there is a problem in which the size of the cardiac cavity represented in the image significantly differs from the size of the actual cardiac cavity.

Furthermore, in setting of the plane from the central axis toward the myocardium, a plane intersecting the myocardium is set with reference to a point on the central axis. Thus, since the plane intersecting the myocardium is set with reference to only the point set on the central axis, it is difficult to set the plane to a desired position of the myocardium. Accordingly, it is difficult to observe a desired cross-section of the myocardium. That is to say, despite observation of a desired cross-section of the myocardium, the plane is set with reference to a point on the central axis set in the cardiac cavity away from the myocardium, and therefore, it is difficult to set the plane to a desired position of the myocardium.

SUMMARY OF THE INVENTION

An object of the present invention is to provide an ultrasonic image processing apparatus capable of generating and displaying an image along the wall-thickness direction of the myocardium, and a method for processing an ultrasonic image.

In a first aspect of the present invention, an ultrasonic image processing apparatus comprises: a contour specifying part configured to receive volume data representing a subject acquired by transmission of ultrasonic waves to the subject and specify a 3-dimensional contour of a myocardium based on the volume data; a forming part configured to set a reference point on the contour of the myocardium and form an image generation plane including a plane substantially orthogonal to the contour of the myocardium at the reference point; an image generator configured to generate image data on the image generation plane based on the volume data; and a display controller configured to control a display to display an image based on the image data.

According to the first aspect, it is possible to generate and display an image along the wall-thickness direction of the myocardium, by forming an image generation plane extending in a direction substantially orthogonal to the contour of the myocardium and generating image data on the image generation plane.

Moreover, since the image generation plane is formed by setting a reference point on the contour of the myocardium, it is possible to set the image generation plane at a desired position of the myocardium and observe a desired cross-section. That is to say, since the image generation plane is set with reference to the myocardium of an observation target, it is possible to set the image generation plane at a desired position of the myocardium and observe a desired cross-section.

Further, in a second aspect of the present invention, a method for processing an ultrasonic image comprises: receiving volume data indicating a subject acquired by transmission of ultrasonic waves to the subject, and specifying a 3-dimensional contour of a myocardium based on the volume data; setting a reference point on the contour of the myocardium, and forming an image generation plane including a plane substantially orthogonal to the contour of the myocardium at the reference point; generating image data on the image generation plane based on the volume data; and displaying an image based on the image data.

BRIEF DESCRIPTION OF THE DRAWINGS

FIG. 6 is a flow chart for describing a series of operations of the ultrasonic imaging apparatus according to the embodiment of the present invention.

FIG. 7 is a view of a screen illustrating an example of an image displayed on the display in a first modification.

DETAILED DESCRIPTION OF THE EMBODIMENTS

Figure 1:
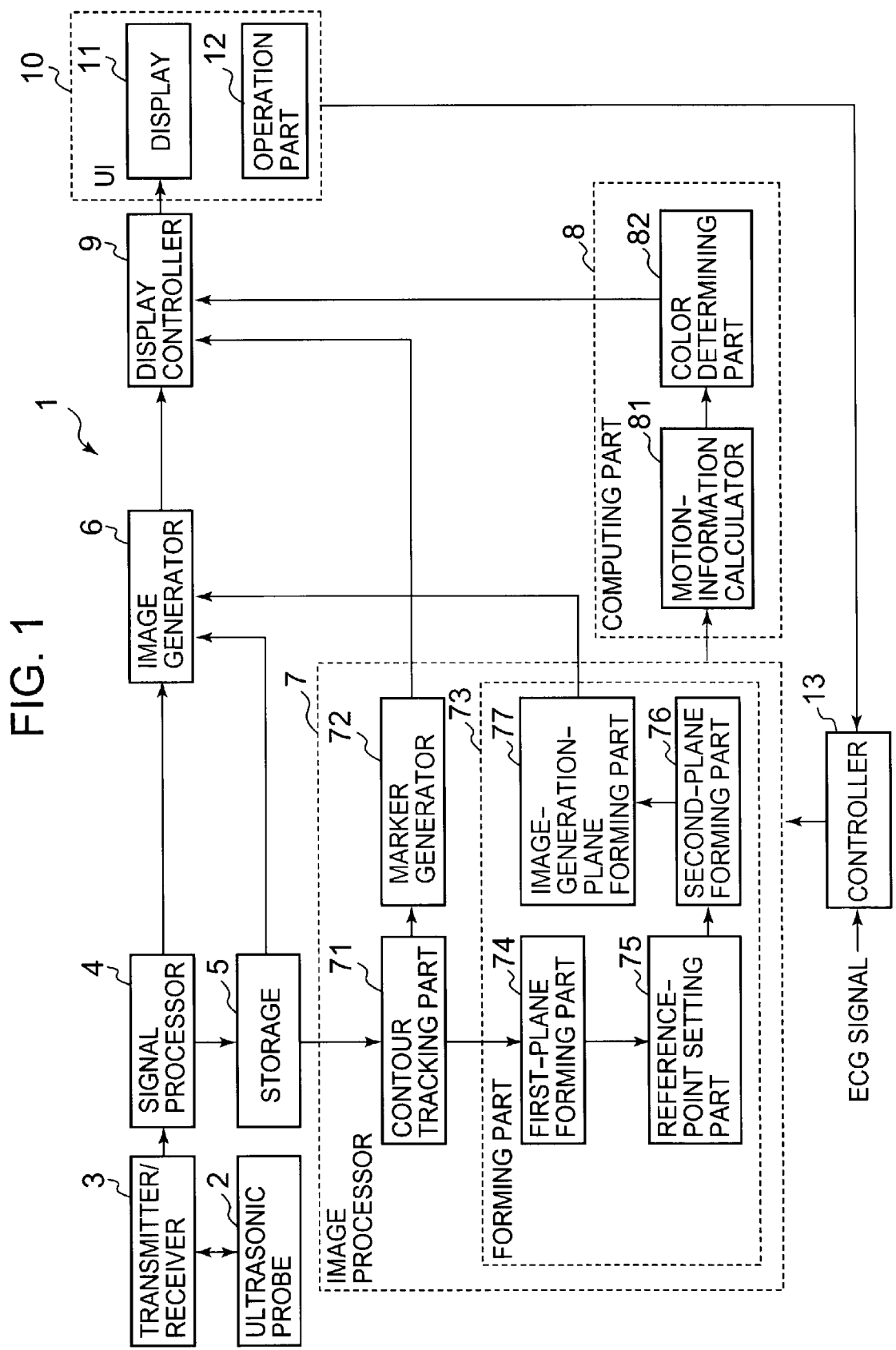
FIG. 1 is a block diagram illustrating an ultrasonic imaging apparatus according to an embodiment of the present invention.

An ultrasonic imaging apparatus according to an embodiment of the present invention will be described with reference to FIG. 1. FIG. 1 is a block diagram illustrating the ultrasonic imaging apparatus according to the embodiment of the present invention.

An ultrasonic imaging apparatus 1 comprises an ultrasonic probe 2, a transmitter/receiver 3, a signal processor 4, a storage 5, an image generator 6, an image processor 7, a computing part 8, a display controller 9, a user interface (UI) 10, and a controller 13. Moreover, an ultrasonic image processing apparatus is composed of the storage 5, the image processor 7, the computing part 8, the display controller 9, the user interface (UI) 10, and the controller 13.

As the ultrasonic probe 2, a 1D array probe in which a plurality of ultrasonic transducers are aligned in a specified direction (a scanning direction), or a 2D array probe in which a plurality of ultrasonic transducers are 2-dimensionally arranged is used.

Alternatively, a 1D array probe in which ultrasonic transducers are aligned in a specified direction (a scanning direction) and the ultrasonic transducers can be mechanically oscillated in a direction (an oscillation direction) orthogonal to the scanning direction may be used.

The transmitter/receiver 3 includes a transmitter and a receiver.

The transmitter/receiver 3 supplies electrical signals to the ultrasonic probe 2 to generate ultrasonic waves and receives echo signals received by the ultrasonic probe 2.

The transmitter of the transmitter/receiver 3 includes a clock generation circuit, a transmission delay circuit, and a pulsar circuit (not shown). The clock generation circuit generates a clock signal that determines the transmission timing and transmission frequency of ultrasonic waves. The transmission delay circuit delays at the time of transmission of ultrasonic waves to execute transmission focus. The pulsar circuit has the same number of pulsars as individual channels corresponding to the respective ultrasonic transducers, and generates a driving pulse at the delayed transmission timing to supply an electrical signal to each of the ultrasonic transducers of the ultrasonic probe 2.

The receiver of the transmitter/receiver 3 includes a preamplifier circuit, an A/D conversion circuit, a reception delay circuit, and an adder circuit. The preamplifier circuit amplifies the echo signal outputted from each of the ultrasonic transducers of the ultrasonic probe 2 at each reception channel. The A/D conversion circuit executes A/D conversion of the amplified echo signal. The reception delay circuit gives a delay time necessary for determination of the transmission directionality to the echo signal after the A/D conversion. The adder circuit adds the delayed echo signals. A reflection component from a direction according to the transmission directionality is emphasized by the addition. Signals after execution of the adding process by the transmitter/receiver 3 may be referred to as "RF data (raw data)." The transmitter/receiver 3 outputs the RF data to the signal processor 4.

The ultrasonic probe 2 and the transmitter/receiver 3 compose an example of an imaging part.

The signal processor 4 includes a B-mode processor, a CFM processor, etc. The B-mode processor images amplitude information of the echo. To be specific, the B-mode processor executes a band pass filter process on the received signals outputted from the transmitter/receiver 3, and thereafter, detects the envelope of the outputted signals. Then, the B-mode processor executes a compression process by logarithmic conversion on the detected data, thereby imaging the amplitude information of the echo. Moreover, the CFM processor images moving blood-flow information. The blood-flow information is information such as the velocity, dispersion and power, and is obtained as binary information.

The signal processor 4 outputs data after execution of signal processing to the storage 5 and the image processor 7. The storage 5 receives the data from the signal processor 4 and stores the data.

Moreover, when volume scan is executed by the ultrasonic probe 2 and the transmitter/receiver 3, the signal processor 4 outputs the volume data acquired by the volume scan to the storage 5 and the image processor 7. The storage 5 receives the volume data from the signal processor 4 and stores the volume data.

The image generator 6 converts the data after signal processing into data of coordinates based on space coordinates (digital scan conversion). For example, the image generator 6 executes a scan conversion process on the data after signal processing outputted from the B-mode processor, thereby generating B-mode image data representing the shape of the tissue of a subject.

When the volume scan is executed by the ultrasonic probe 2 and the transmitter/receiver 3, the image generator 6 receives the volume data from the signal processor 4 and executes volume rendering on the volume data, thereby generating 3-dimensional image data that sterically represents the tissues. Moreover, the image generator 6 may execute the MPR (Multi Planar Reconstruction) process on the volume data to generate image data (MPR image data) in an arbitrary cross-section. Then, the image generator 6 outputs ultrasonic image data such as 3-dimensional image data and MPR image data to the display controller 9.

When an ECG (electrocardiogram) signal of a subject is already acquired, the controller 13 receives the ECG signal from outside the ultrasonic imaging apparatus 1, correlates a cardiac phase received at the timing of acquisition of volume data to the volume data, and controls the storage 5 to store.

The ultrasonic imaging apparatus 1 according to the present embodiment scans the heart of the subject with ultrasonic waves, thereby acquiring volume data representing the heart in each cardiac phase. Specifically, the ultrasonic imaging apparatus 1 acquires moving image data of the heart. For example, the ultrasonic imaging apparatus 1 scans the heart of the subject with ultrasonic waves for one cardiac cycle or more, thereby acquiring a plurality of volume data (moving image data) for one cardiac cycle or more. Moreover, when the ECG signal is already acquired, the controller 13 relates a cardiac phase received at the timing of acquisition of each volume data to the volume data, and controls the storage 5 store. Consequently, a cardiac phase in which each of the plurality of volume data has been acquired is related to the volume data and stored in the storage 5.

The display controller 9 receives the MPR image data or 3-dimensional image data from the image generator 6, and controls a display 11 to display an MPR image or a 3-dimensional image. For example, when the operator designates an arbitrary cardiac phase by using the operation part 12, the image generator 6 generates MPR image data or 3-dimensional image data based on volume data correlated to the designated cardiac phase, and the display controller 9 controls the display 11 to display an MPR image or 3-dimensional image in the cardiac phase.

For example, the image generator 6 generates MPR image data (hereinafter may be referred to as "long-axis image data") in a cross-section (hereinafter may be referred to as "long-axis cross-section") along the cardiac long-axis direction, or MPR image data (hereinafter may be referred to as "short-axis image data") in a cross-section (hereinafter may be referred to as "short-axis cross-section") along the cardiac short-axis direction. Then, the display controller 9 controls the display 11 to display a long-axis image based on the long-axis image data or a short-axis image based on the short-axis image data.

The image processor 7 includes a contour tracking part 71, a marker generator 72, and a forming part 73. The contour tracking part 71 specifies the contour of a myocardium based on volume data that shows the heart. Specifically, the contour tracking part 71 specifies the position of the endocardium and the position of the epicardium of the heart. Then, the contour tracking part 71 executes pattern matching on the two volume data acquired in different cardiac phases, thereby obtaining the position of the contour of the myocardium in each cardiac phase. Specifically, the contour tracking part 71 obtains the position of the endocardium and the position of the epicardium by pattern matching.

For example, the contour tracking part 71 reads out volume data from the storage 5, and detects the boundary between a tissue area and a blood area based on the luminance value of each of pixels composing the volume data. In the present embodiment, the contour tracking part 71 detects a 3-dimensional contour of the endocardium and a 3-dimensional contour of the epicardium of the heart. The contour tracking part 71 reads out volume data acquired in a preset cardiac phase from the storage 5, and detects the 3-dimensional contour of the myocardium based on the luminance distribution of the volume data.

Specifically, the contour tracking part 71 detects the 3-dimensional contour of the endocardium and the 3-dimensional contour of the epicardium based on the luminance values of the volume data. This preset cardiac phase can be changed to any cardiac phase by the operator. For example, the contour tracking part 71 reads out volume data acquired during the end diastole (a cardiac phase in which R-waves have been detected) or volume data acquired during the end systole (a cardiac phase after a lapse of a specified time from the cardiac phase in which the R-waves have been detected) from the storage 5. Then, the contour tracking part 71 detects the 3-dimensional contour of the endocardium and the 3-dimensional contour of the epicardium based on the read-out volume data. Volume data is correlated to a cardiac phase in which the volume data has been acquired, and stored in the storage 5. Thus, the contour tracking part 71 reads out volume data acquired in a cardiac phase such as the end diastole and the end systole, and detects the 3-dimensional contour of the endocardium and the 3-dimensional contour of the epicardium in the cardiac phase. This detected 3-dimensional contour of the myocardium is set in the contour tracking part 71 as an initial contour of the myocardium of a tracking target. For example, a 3-dimensional contour of the myocardium in the cardiac phase in which the R-waves have been detected is set in the contour tracking part 71 as the initial contour.

Further, the contour tracking part 71 may obtain a normal vector at each position on the detected endocardium and define a position that is a certain distance outside from each position on the endocardium in the direction of the normal vector, as the 3-dimensional contour of the epicardium of the heart. For example, the contour tracking part 71 defines a position 8 mm outside from the position on the endocardium, as the contour of the epicardium. This certain distance can be changed to any value by the operator. When the 3-dimensional contour of the epicardium is thus detected, the contour is set in the contour tracking part 71 as the initial contour of the epicardium to track. For example, the 3-dimensional contour of the epicardium in a cardiac phase when R-wave has been detected is set in the contour tracking part 71 as the initial contour.

As described above, when the 3-dimensional contour of the myocardium in a specific cardiac phase (the initial contour) is detected, the contour tracking part 71 executes pattern matching using a speckle pattern on two images. Through this pattern matching, the contour tracking part 71 obtains the position of each of the points composing the 3-dimensional contour of the myocardium set as the initial contour, for each volume data generated in each cardiac phase. That is, the contour tracking part 71 obtains the position of each point on the 3-dimensional contour of the endocardium and the position of each point on the 3-dimensional contour of the epicardium, for each volume data acquired in each cardiac phase. Then, the contour tracking part 71 temporally tracks each of the points composing the 3-dimensional contour of the endocardium and each of the points composing the 3-dimensional contour of the epicardium.

For example, the contour tracking part 71 receives coordinate information of each of the points composing the contour of the endocardium set as the initial contour, and coordinate information of each of the points composing the contour of the epicardium. In addition, the contour tracking part 71 reads out volume data (hereinafter referred to as the "volume data B") acquired in a cardiac phase following the volume data (hereinafter referred to as the "volume data A") from which the initial contour has been detected, from the storage 5. Then, the contour tracking part 71 executes pattern matching using a speckle pattern on the two volume data that are temporally consecutive.

Through this pattern matching, the contour tracking part 71 obtains a motion vector of each of the points composing the contour of the myocardium set as the initial contour. That is, the contour tracking part 71 obtains the motion vector of each of the points on the contour of the endocardium and the motion vector of each of the points on the contour of the epicardium through this pattern matching. To be specific, the contour tracking part 71 executes pattern matching using a speckle pattern on the volume data A and the volume data B, thereby obtaining the motion vector of each of the points composing the contour of the endocardium and the motion vector of each of the points composing the contour of the epicardium. This motion vector represents the displacement of each of the points composing the contour and the movement direction in which each of the points has been displaced. In short, the contour tracking part 71 executes pattern matching on the two volume data and calculates the movement amount of the speckle, thereby obtaining the motion vector of each of the points composing the contour. By obtaining the motion vector of each of the points composing the contour in this manner, the position of each of the points composing the contour of the myocardium in the cardiac phase in which the volume data B has been generated is obtained.

In addition, the contour tracking part 71 reads out volume data (hereinafter referred to as the "volume data C") acquired in a cardiac phase following the volume data B, from the storage 5. Then, the contour tracking part 71 executes pattern matching using a speckle pattern on the two volume data (volume data B and volume data C) that are temporally consecutive, thereby obtaining a motion vector of each of the points composing the contour of the myocardium. Consequently, the position of each of the points composing the contour of the myocardium in the cardiac phase in which the volume data C has been acquired is obtained.

Thus, the contour tracking part 71 executes pattern matching using a speckle pattern, thereby obtaining the motion vector of each of the points composing the contour of the myocardium set as the initial contour, in each cardiac phase in which each volume data has been acquired. Consequently, the contour tracking part 71 temporally tracks the motion vector of each of the points composing the contour of the myocardium. As a result, it becomes possible to temporally track each of the points composing the 3-dimensional contour of the myocardium.

For example, the contour tracking part 71 obtains the position of each of the points composing the 3-dimensional contour of the myocardium in each cardiac phase, for all volume data acquired in one cardiac cycle. Consequently, the position of each of the points composing the 3-dimensional contour of the myocardium in each cardiac phase is obtained for one cardiac cycle. The contour tracking part 71 is equivalent to an example of the "contour specifying part" of the present invention.

The contour tracking part 71 outputs coordinate information of each of the points composing the 3-dimensional contour of the endocardium in each cardiac phase, and coordinate information of each of the points composing the 3-dimensional contour of the epicardium in each cardiac phase, to the forming part 73 and the computing part 8.

Below, the forming part 73 and the computing part 8 will be described.

Figure 2:
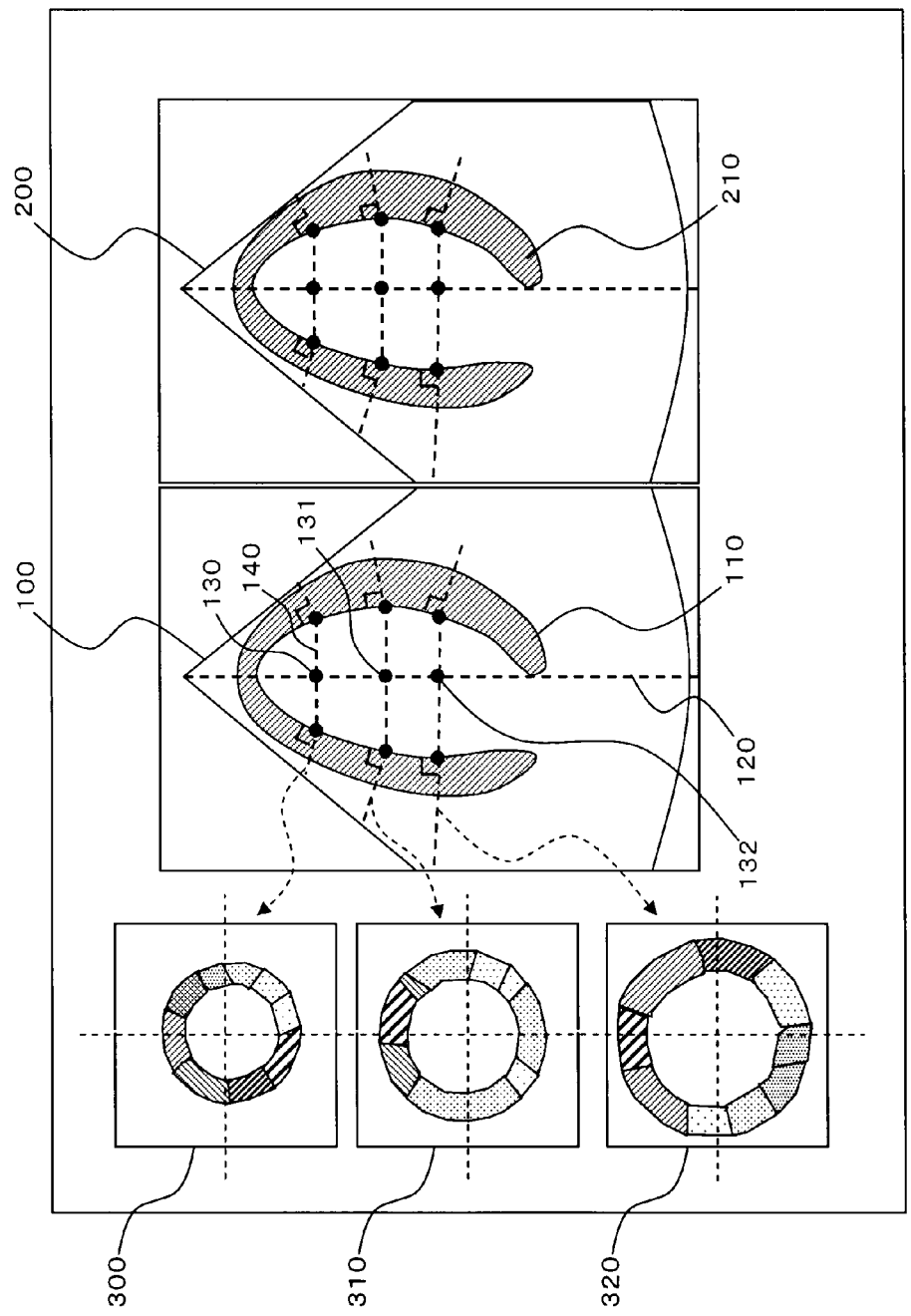
FIG. 2 is a view of a screen illustrating an example of an image displayed on a display.
Figure 3:
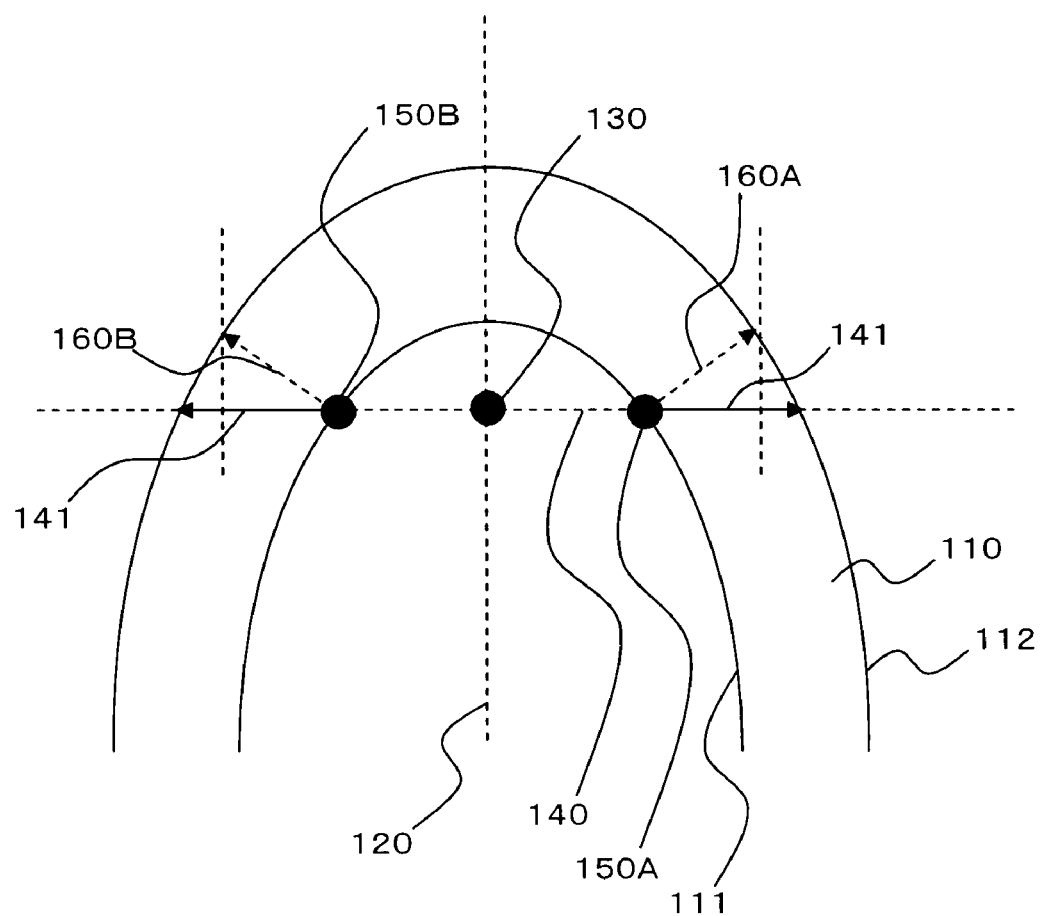
FIG. 3 is a schematic view illustrating the contour of a myocardium in a cross-section along the long-axis direction of the myocardium.
Figure 4:
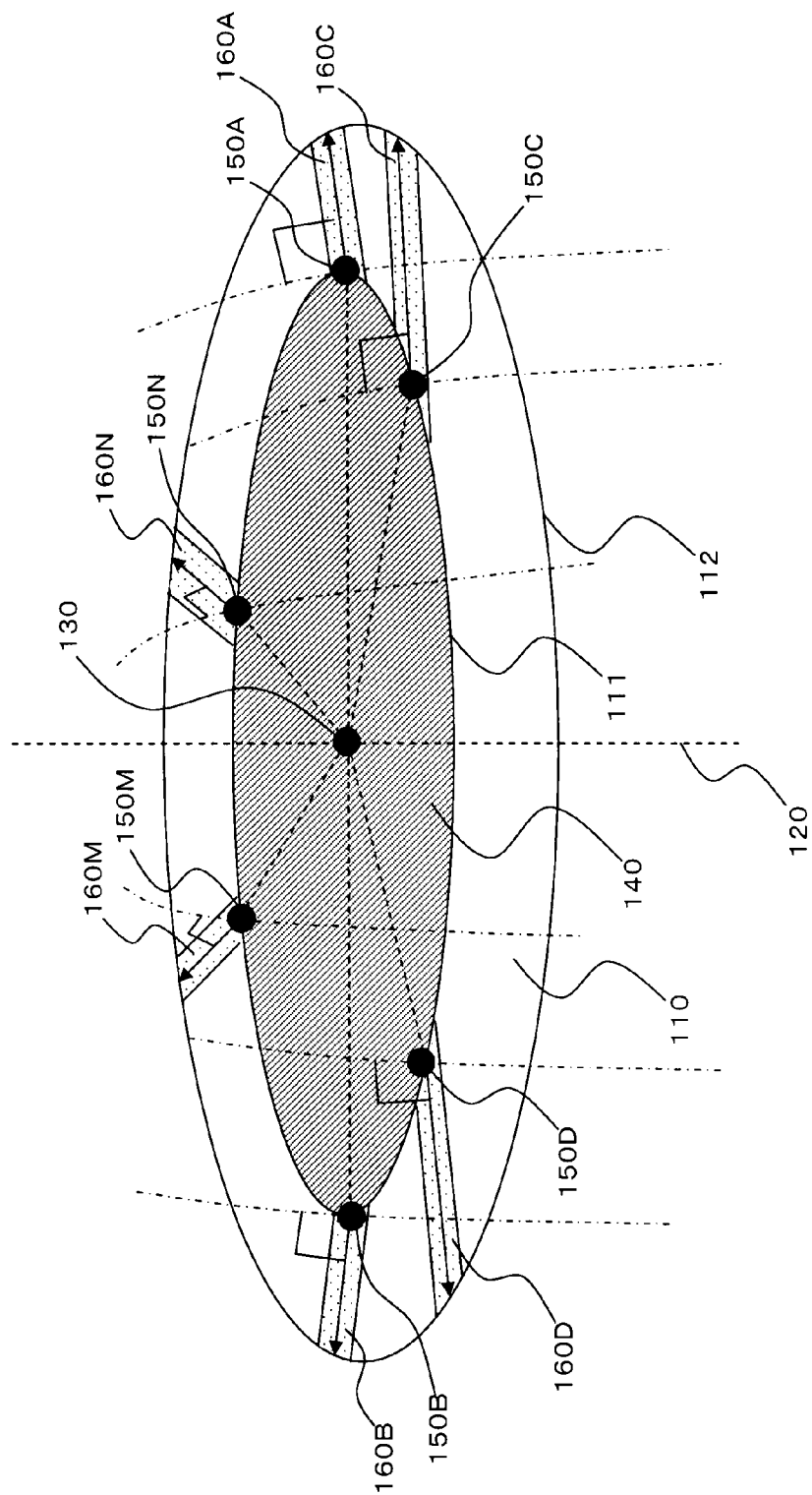
FIG. 4 is a schematic view illustrating the contour of a myocardium in a cross-section along the short-axis direction of the myocardium.

Firstly, the processing by the forming part 73 will be described referring to FIGS. 2 through 4. FIG. 2 is a view of a screen showing an example of an image displayed on the display. FIG. 3 is a schematic view showing the contour of a myocardium in a cross-section along the long-axis direction of the myocardium. FIG. 4 is a schematic view showing the contour of a myocardium in a cross-section along the short-axis direction of the myocardium.

The forming part 73 includes a first-plane forming part 74, a reference-point setting part 75, a second-plane forming part 76, and an image-generation-plane forming part 77. The forming part 73 obtains a plane orthogonal to the myocardium based on the 3-dimensional contour of the myocardium obtained by the contour tracking part 71.

The image generator 6 generates MPR image data of the plane.

The processing by the forming part 73 will be described below in detail.

The image generator 6 generates MPR image data in an arbitrary cross-section based on volume data acquired in an arbitrary cardiac phase. For example, the operator designates an arbitrary cardiac phase by using the operation part 12, and further designates an arbitrary cross-section for the volume data. The cardiac phase designated with the operation part 12 and coordinate information of the cross-section in the 3-dimensional space are outputted from the user interface 10 (U1) to the controller 13. The controller 13 then outputs the cardiac phase and the coordinate information in the cross-section to the image generator 6.

As an example, the operator designates a cross-section along the long-axis direction of a heart by using the operation part 12. The image generator 6 reads out the volume data correlated with the designated cardiac phase from the storage 5. The image generator 6 then generates MPR image data (long-axis image data) in the cross-section in the long-axis direction of the heart, based on the read-out volume data.

The display controller 9 receives the long-axis image data from the image generator 6, and controls the display 11 to display a long-axis image based on the long-axis image data. The image generator 6 may generate MPR image data (long-axis image data) in a cross-section in the long-axis direction that is a cross-section orthogonal to the cross-section designated by the operator.

An example of the long-axis image displayed on the display 11 is shown in FIG. 2. The display controller 9 controls the display 11 to display a long-axis image 100 of the heart, and a long-axis image 200 in a cross-section orthogonal to the long-axis image 100. In the long-axis image 100, a myocardium 110 on a long-axis cross-section is shown. Similarly, in the long-axis image 200, a myocardium 210 on a long-axis cross-section is shown. In the example shown in FIG. 2, the long-axis image 100 and the long-axis image 200 are displayed on the display 11, but it is also possible to display only one long-axis image.

Then, the operator designates a reference axis for the long-axis image 100 by using the operation part 12. The display controller 9 controls the display 11 to display a reference axis 120 designated by the operator. For example, a central axis that passes through the center of the long-axis image 100 along the long-axis direction of the long-axis image 100 is designated as the reference axis 120. In addition, the operator designates an arbitrary point on the reference axis 120 by using the operation part 12. For example, as shown in FIGS. 2 and 3, the operator designates a point 130 on the reference axis 120 by using the operation part 12.

Then, coordinate information of the reference axis 120 on the long-axis image 100 is outputted from the user interface (UI) 10 to the controller 13. In addition, coordinate information of the point 130 on the long-axis image 100 is outputted from the user interface (UI) 10 to the controller 13. Since the coordinate information in the 3-dimensional space of the long-axis cross-section in which the long-axis image 100 has been generated is already outputted to the controller 13, the coordinates of the reference axis 120 and the point 130 in the 3-dimensional space are specified in the controller 13. The controller 13 outputs the coordinate information of the reference axis 120 and the coordinate information of the point 130 in the 3-dimensional space, to the forming part 73.

The first-plane forming part 74 receives the coordinate information of each of the points composing the contour of the myocardium in the cardiac phase designated by the operator, from the contour tracking part 71, and sets the reference axis 120 and the point 130 on the contour of the myocardium. The first-plane forming part 74 then forms a first plane 140 passing through the point 130 and orthogonal to the reference axis 120, as shown in FIG. 4. Then, the first-plane forming part 74 outputs coordinate information of the first plane 140 in the 3-dimensional space, to the reference-point setting part 75.

The reference-point setting part 75 receives the coordinate information of the first plane 140 from the first-plane forming part 74 and obtains points where the contour of the myocardium intersects the first plane 140. For example, as shown in FIG. 4, the reference-point setting part 75 obtains points where the contour of an endocardium 111 and the first plane 140 intersect each other, and sets the intersecting points as reference points. At this moment, the reference-point setting part 75 obtains points that intersect the contour of the endocardium 111 in a 360-degree periphery within the first plane 140. In the example shown in FIG. 4, the reference-point setting part 75 obtains a plurality of reference points 150A, 150B . . . 150N . . . where the first plane 140 and the contour of the endocardium 111 intersect each other. The reference-point setting part 75 then outputs coordinate information of the reference points to the second-plane forming part 76.

The reference-point setting part 75 may obtain points where the first plane 140 and the contour of not the endocardium 111 but an epicardium 112 intersect each other, and sets the points as the reference points.

The second-plane forming part 76 receives the coordinate information of the reference points from the reference-point setting part 75, and forms a second plane extending in a direction orthogonal to the contour of the endocardium 111 within the long-axis cross-section with reference to each of the reference points. This second plane has a specified width in the circumferential direction of the endocardium. For example, as shown in FIG. 3 and FIG. 4, the second-plane forming part 76 forms a second plane 160A extending in a direction orthogonal to the contour of the endocardium 111 within the long-axis cross-section with reference to the point 150A. Similarly, the second-plane forming part 76 forms a second plane 160B extending in a direction orthogonal to the contour of the endocardium 111 within the long-axis cross-section with reference to the reference point 150B. As shown in FIG. 4, the second-plane forming part 76 then forms second planes 160A . . . 160N . . . extending in a direction orthogonal to the contour of the endocardium 111 for the respective reference points 150A . . . 150N . . . obtained in a 360-degree periphery within the first plane 140. The second plane is orthogonal to the contour of the endocardium 111, and therefore, is parallel to the wall-thickness direction of the myocardium 110. The second-plane forming part 76 then outputs the coordinate information of the second planes to the image-generation-plane forming part 77.

The image-generation-plane forming part 77 receives the coordinate information of the first plane from the first-plane forming part 74, receives the coordinate information of the second planes from the second-plane forming part 76, and connects the first plane with the second planes at the reference points where the first plane and the contour of the endocardium intersect each other. The image-generation-plane forming part 77 forms an image generation plane through this connection. To be specific, the image-generation-plane forming part 77 forms an image generation plane by connecting the first plane formed inside the endocardium 111 (in the cardiac cavity) with the second planes formed outside the endocardium 111 at the reference points where the first plane and the contour of the endocardium intersect each other. Consequently, the image generation plane is composed of the first plane inside the endocardium 111 (in the cardiac cavity) and the second planes outside the endocardium 111. In the example shown in FIG. 4, the image-generation-plane forming part 77 forms one image generation plane by connecting the first plane 140 formed inside the endocardium 111 (in the cardiac cavity) with the second planes 160A . . . 160N . . . formed outside the endocardium 111 at the reference points 150A . . . 150N . . ., respectively. The image-generation-plane forming part 77 then outputs coordinate information of the image generation plane to the image generator 6.

The image generator 6 reads out the volume data acquired in the cardiac phase designated by the operator, from the storage 5. The image generator 6 then generates MPR image data on the image generation plane formed by the image-generation-plane forming part 77 by executing the MPR process on the volume data. Consequently, MPR image data on the image generation plane composed of the first plane 140 and the second planes 160A . . . 160N . . . is generated. The image generator 6 outputs the MPR image data on the image generation plane to the display controller 9.

Upon receiving the MPR image data on the image generation plane from the image generator 6, the display controller 9 controls the display 11 to display an MPR image based on the MPR image data.

This MPR image represents a short-axis image of the heart.

The image generator 6 may generate MPR image data on the image generation plane formed by the image-generation-plane forming part 77 in each cardiac phase by reading out the volume data acquired in each cardiac phase from the storage 5 and executing the MPR process on the volume data acquired in each cardiac phase. In this case, upon receiving the MPR image data in each cardiac phase from the image generator 6, the display controller 9 controls the display 11 to display an MPR image in each cardiac phase sequentially in each cardiac phase.

Here, a difference between the ultrasonic imaging apparatus 1 according to the present embodiment and the conventional technique will be described with reference to FIG. 3. In the conventional technique, MPR image data on a plane in which the myocardium 110 is cut by the first plane 140 is generated. In other words, a plane intersecting the myocardium 110 is obtained by extending the first plane 140, and MPR image data is generated on the intersecting plane.

Therefore, in the myocardium 110, MPR image data on a plane 141 along a direction different from the wall-thickness direction of the myocardium 110 is generated. On the other hand, in the present embodiment, in the myocardium 110, a plane such as the second plane 160A orthogonal to the myocardium 110 is obtained, and MPR image data on the plane such as the second plane 160A is generated. Thus, in the myocardium 110, MPR image data on the plane along the wall-thickness direction of the myocardium is generated. Consequently, according to the present embodiment, it becomes possible to observe a cross-section along the wall-thickness direction in the myocardium 110.

Furthermore, short-axis image data along the wall-thickness direction can be obtained just by the operator designating an arbitrary point on the long-axis image. Thus, it becomes possible to observe a cross-section having a desired wall thickness with a simple operation.

Moreover, in the cardiac cavity, short-axis image data on the first plane orthogonal to the reference axis 120 is generated. Thus, the shape of the cardiac cavity represented in the short-axis image does not differ significantly from the actual shape of the cardiac cavity. For example, the size of the cardiac cavity represented in the short-axis image does not differ significantly from the actual size of the cardiac cavity.

Furthermore, since the first plane passing through the point set on the reference axis and orthogonal to the reference axis is set, and the second planes orthogonal to the myocardium are set with reference to positions where the first plane and the myocardium intersect each other, it is possible to easily set the second planes to desired positions of the myocardium. That is, since the second planes are set with reference to the myocardium to be observed, it becomes possible to set the second planes to desired positions of the myocardium to observe the desired cross-section. In the conventional technique, a plane orthogonal to the myocardium is set with reference to a point set on the reference axis to generate image data of the plane, so that it is difficult to set the plane to a desired position of the myocardium. On the other hand, in the present embodiment, points where the first plane and the myocardium intersect each other are obtained and second planes orthogonal to the myocardium are set with reference to points to generate image data of those second planes. Accordingly, it becomes possible to easily observe the desired cross-section of the myocardium.

Next, the computing part 8 will be described. The computing part 8 receives the coordinate information of each of the points composing the 3-dimensional contour of the myocardium in each cardiac phase from the contour tracking part 71, and obtains wall motion information of the myocardium. For example, the computing part 8 obtains displacement of the endocardium and displacement of the epicardium in each cardiac phase and obtains the strain of the myocardium in each cardiac phase based on these displacements. In addition, the computing part 8 may obtain a strain rate that indicates the temporal change rate of the strain. Thus, it is possible to perform evaluation of the heart by obtaining wall motion information such as displacement, strain or a strain rate. Since the contour of the myocardium is tracked 3-dimensionally by the contour tracking part 71, the contour of the myocardium is defined by 3-dimensional coordinates.

Therefore, the wall motion information obtained by the computing part 8 is also defined by 3-dimensional coordinates.

Consequently, the wall motion information on an arbitrary plane of the heart can be obtained. Below, the function of each of parts composing the computing part 8 will be described. The computing part 8 includes a motion-information calculator 81 and a color determining part 82.

For example, the motion-information calculator 81 obtains displacement of the endocardium and displacement of the epicardium in each cardiac phase, based on the coordinate information of each of the points composing the 3-dimensional contour of the myocardium in each cardiac phase. As an example, the motion-information calculator 81 obtains displacement of the endocardium and displacement of the epicardium with respect to the long-axis direction and the short-axis direction of the heart.

Then, the motion-information calculator 81 obtains the strain of the myocardium with respect to the long-axis direction and the short-axis direction of the heart in each cardiac phase, based on the displacement of the myocardium in each cardiac phase. For example, a cardiac phase in which R-wave has been detected is set as the initial time phase. The motion-information calculator 81 compares the 3-dimensional contour of the endocardium in the initial time phase with the 3-dimensional contour of the endocardium in another cardiac phase, and obtains the displacement of the endocardium with respect to the long-axis direction and the short-axis direction of the heart in each cardiac phase. Similarly, the motion-information calculator 81 compares the 3-dimensional contour of the epicardium in the initial time phase with the 3-dimensional contour of the epicardium in another cardiac phase, and obtains the displacement of the epicardium with respect to the long-axis direction and the short-axis direction of the heart in each cardiac phase. Then, the motion-information calculator 81 obtains the strain in each cardiac phase based on the displacement in each cardiac phase.

Here, as an example of the strain, a case of obtaining the strain in the thickness direction (wall-thickness direction) between the endocardium and the epicardium will be described. As described above, when the 3-dimensional contour of the endocardium and the 3-dimensional contour of the epicardium in each cardiac phase is already obtained, the motion-information calculator 81 obtains the strain in the wall-thickness direction in each cardiac phase, based on the coordinate information of each of the points composing the 3-dimensional contour of the endocardium in each cardiac phase and the coordinate information of each of the points composing the 3-dimensional contour of the contour of the epicardium in each cardiac phase. Here, the strain in the wall-thickness direction is defined as the strain in the thickness direction between the endocardium and the epicardium.

For example, the motion-information calculator 81 obtains a line orthogonal to the contour of the endocardium at a point on the contour of the endocardium. Then, the motion-information calculator 81 obtains a point where the orthogonal line intersects the contour of the epicardium. The motion-information calculator 81 obtains the strain (strain in the wall-thickness direction) between the endocardium and the epicardium in each cardiac phase based on the distance between the point on the contour of the endocardium and the point on the contour of the epicardium in each cardiac phase.

For example, a cardiac phase in which the initial contours of the endocardium and epicardium have been set is set as the initial time phase. A distance between a point on the endocardium and a point on the epicardium in the initial time phase will be a distance $L(0)$. To be specific, in a case where the initial contours of the endocardium and epicardium are designated in a cardiac phase in which R-waves have been detected, the cardiac phase in which the R-waves have been detected is the initial time phase. Moreover, a distance between a point on the endocardium and a point on the epicardium in an arbitrary cardiac phase will be a distance $L(t)$.

Then, the motion-information calculator 81 receives the coordinate information of each of the points composing the 3-dimensional contour of the endocardium and the coordinate information of each of the points composing the 3-dimensional contour of the epicardium in each cardiac phase from the contour tracking part 71, and obtains a difference $\Delta L(t)$ between the distance $L(t)$ in an arbitrary cardiac phase and the distance $L(0)$ in the initial time phase.

This difference $\Delta L(t)$ is equivalent to the displacement of the membrane thickness. Next, the motion-information calculator 81 obtains strain $S(t)$ in the wall-thickness direction in an arbitrary cardiac phase by dividing the difference $\Delta L(t)$ by the distance $L(0)$ in the initial time phase.

The motion-information calculator 81 obtains the strain $S(t)$ in the wall-thickness direction at specified intervals at the contour of the endocardium and the contour of the epicardium. That is, the motion-information calculator 81 obtains the strain $S(t)$ at a plurality of sites of the endocardium and the epicardium. Thus, the motion-information calculator 81 obtains the strain $S(t)$ in the wall-thickness direction at each site of the myocardium in each cardiac phase.

The motion-information calculator 81 may obtain a strain rate (velocity) $SR(t)$ that indicates the temporal change rate of the strain $S(t)$ in each cardiac phase, by temporally differentiating the strain $S(t)$ in the wall-thickness direction at each site in each cardiac phase.

The motion-information calculator 81 may obtain the displacement and strain (change rate of displacement) in the circumferential direction (tangential direction of the contour) of the myocardium in each cardiac phase, based on the coordinate information of each of the points composing the 3-dimensional contours of the myocardium in each cardiac phase.

The color determining part 82 determines a color corresponding to the magnitude of the strain $S(t)$ at each site obtained by the motion-information calculator 81. The color determining part 82 then assigns a color that differs depending on the magnitude of the strain $S(t)$, to each site. For example, a color to be assigned to each magnitude of the strain $S(t)$ is previously determined. Subsequently, a table in which the magnitude of the strain $S(t)$ is correlated with a color is previously created and stored in a storage (not shown). In this table, different colors are assigned according to the magnitude of the strain $S(t)$. The color determining part 82 determines a color corresponding to the magnitude of the strain $S(t)$ at each site in each cardiac phase with reference to the table. The color determining part 82 then outputs coordinate information at each site in each cardiac phase and information that indicates the color assigned to the site (color information) to the display controller 9.

In the present embodiment, the image-generation-plane forming part 77 outputs the coordinate information of the image generation plane composed of the first plane and the second planes, to the color determining part 82. The color determining part 82 receives the coordinate information of the image generation plane from the image-generation-plane forming part 77, and determines a color corresponding to the magnitude of the wall motion information at each site on the image generation plane. For example, the color determining part 82 determines a color corresponding to the magnitude of the strain $S(t)$ at each site on the image generation plane, and assigns the color to each site. The color determining part 82 then outputs coordinate information at each site on the image generation plane and information that indicates the color assigned to the site (color information), to the display controller 9.

The display controller 9 receives the coordinate information at each site on the image generation plane in the designated cardiac phase and the information that indicates the color assigned to the site (color information), from the color determining part 82. Then, the display controller 9 controls the display 11 to display in a state that the color assigned by the color determining part 82 is superimposed on each site of the myocardium on the MPR image generated by the image generator 6. At this moment, the display controller 9 controls the display 11 to display in a state that the color assigned to each site is superimposed within a range having a specified width around each site.

Here, the MPR image (short-axis image) generated by the image generator 6 and an example of coloring for the short-axis image will be described with reference to FIG. 2. For example, the display controller 9 controls the display 11 to display a short-axis image 300 on the image generation plane formed with the first plane 140 passing through the point 130 on the reference axis 120 and the second planes 160A . . . 160N . . . orthogonal to the myocardium. The display controller 9 then controls the display 11 to display in a state that a color according to the magnitude of the wall motion information at each site on the image generation plane is superimposed on each site of the short-axis image 300. In the example shown in FIG. 2, colors according to the magnitude of the wall motion information are represented with different types of hatching for descriptive purposes.

Moreover, when the operator designates another point 131 on the reference axis 120 by using the operation part 12, the forming part 73 forms an image generation plane corresponding to point 131. The image generator 6 then generates short-axis image data on the image generation plane corresponding to the point 131. The computing part 8 determines a color according to the magnitude of the wall motion information at each site on the image generation plane, and assigns the color to each site. Then, the display controller 9 controls the display 11 to display a short-axis image 310 on the image generation plane corresponding to the point 131, and controls the display 11 to display in a state that the color according to the magnitude of the wall motion information is superimposed on the short-axis image 310. Moreover, when the point 132 is designated, similarly to the point 130 and point 131, the display controller 9 controls the display 11 to display a short-axis image 320 on the image generation plane corresponding to the point 132. In addition, the display controller 9 controls the display 11 to display in a state that the color according to the magnitude of the wall motion information on the image generation plane is superimposed on the short-axis image 320.

As described above, the ultrasonic imaging apparatus 1 according to the present embodiment generates, in the myocardium 110, MPR image data (short-axis image data) on a plane toward the wall-thickness direction of the myocardium. Therefore, the orientation of the vector of the wall motion information coincides with the wall-thickness direction of the myocardium represented in the short-axis image. Consequently, the actual wall motion information in the short-axis image 300 is displayed in the short-axis image 300. As a result, it is possible to more properly evaluate the wall motion at each part of the myocardium.

Figure 5:
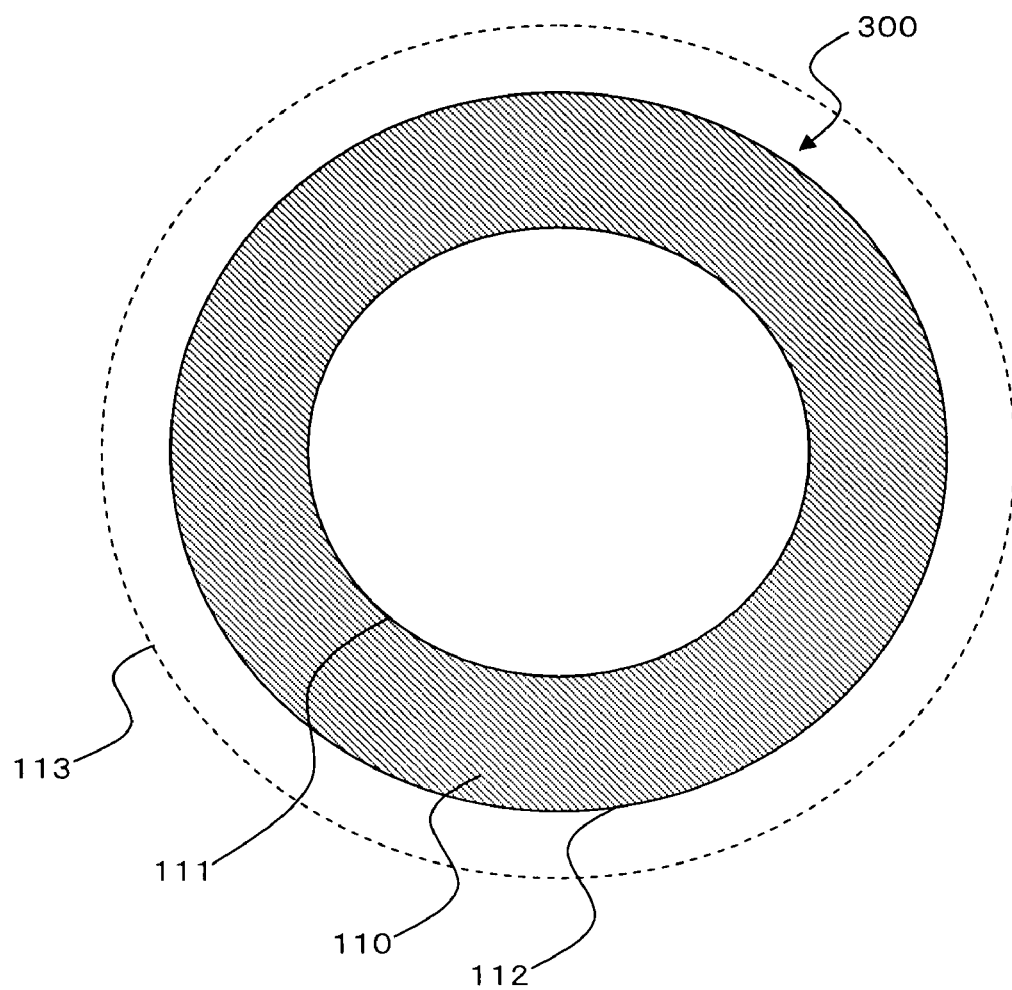
FIG. 5 is a view schematically illustrating a short-axis image.

A difference between the ultrasonic imaging apparatus 1 according to the present embodiment and the conventional technique will be described with reference to FIG. 5. FIG. 5 is a view schematically showing a short-axis image. In the short-axis image 300 according to the present embodiment, the endocardium 111 and the epicardium 112 of the myocardium 110 are represented. On the other hand, in the short-axis image according to the conventional technique, the endocardium 111 and an epicardium 113 of the myocardium 110 are represented. The epicardium 113 according to the conventional technique is represented outside the epicardium 112 according to the short-axis image 300. In the conventional technique, as shown in FIG. 3, MPR image data (short-axis image data) on the plane 141 obtained by cutting the myocardium 110 by the first plane 140 is generated.

Therefore, the thickness of the myocardium (thickness between the endocardium 111 and the epicardium 113) represented in the short-axis image according to the conventional technique is thicker than the thickness in the wall-thickness direction of the myocardium 110. On the other hand, in the present embodiment, as shown in FIGS. 2 through 4, MPR image data (short-axis image data) on a plane obtained by cutting the myocardium 110 by the second plane 160A etc. orthogonal to the myocardium 110 is generated. Therefore, the thickness of the myocardium (thickness between the endocardium 111 and the epicardium 112) represented in the short-axis image 300 coincides with the thickness in the wall-thickness direction of the myocardium 110. Then, the color corresponding to the wall motion information is assigned to each site of the myocardium 110. In the present embodiment, the thickness of the myocardium (thickness between the endocardium 111 and the epicardium 112) represented in the short-axis image 300 coincides with the thickness in the wall-thickness direction of the myocardium 110, and thus, the colors corresponding to the wall motion information are properly assigned to the short-axis image 300 and displayed.

In addition, since different colors are assigned according to the magnitude of the wall motion information and displayed on the display 11, it is possible to easily grasp the decrease or increase in the diastolic function at each site by observing the colors.

The marker generator 72 of the image processor 7 generates markers that indicate 2-dimensional contours of the endocardium and epicardium on the image generation plane formed by the image-generation-plane forming part 77. The display controller 9 then controls the display 11 to display in a state that the markers are superimposed on the short-axis image. This marker generator 72 may be omitted in the ultrasonic imaging apparatus 1 according to the present embodiment.

The user interface (UI) 10 includes the display 11 and the operation part 12. The display 11 is composed of a monitor such as a CRT or liquid crystal display, and an MPR image, a 3-dimensional image, etc. are displayed on the screen. The operation part 12 is composed of a keyboard, a mouse, a trackball, a TCS (Touch Command Screen), etc., and various instructions are given through operation by the operator.

The controller 13 is connected to each part of the ultrasonic imaging apparatus 1, and controls the operation of each part.

The image generator 6 is provided with a CPU (Central Processing Unit) and a storage (not shown) such as a ROM (Read Only Memory), a RAM (Random Access Memory) and an HDD (Hard Disk Drive). An image-generating program for executing the function of the image generator 6 is stored in the storage. By the CPU executing the image-generating program, image processing such as an MPR process and volume rendering is executed on the volume data. Consequently, ultrasonic image data such as MPR image data and 3-dimensional image data is generated.

The image processor 7 is provided with a CPU and a storage (not shown) such as a ROM, a RAM and an HDD. An image processing program for executing the function of each part of the image processor 7 is stored in the storage. The image processing program includes a contour-tracking program for executing the function of the contour tracking part 71, a marker-generating program for executing the function of the marker generator 72, and a forming program for executing the function of the forming part 73. The forming program includes a first-plane forming program for executing the function of the first-plane forming part 74, a reference-point setting program for executing the function of the reference-point setting part 75, a second-plane forming program for executing the function of the second-plane forming part 76, and an image-generation-plane forming program for executing the function of the image-generation-plane forming part 77. By the CPU executing the contour-tracking program, the contour of the myocardium (endocardium and epicardium) in each cardiac phase is obtained. By the CPU executing the marker-generating program, the markers that indicate the contours of the endocardium and epicardium are generated. By the CPU executing the first-plane forming program, the first plane orthogonal to the reference line set for the myocardium is formed. By the CPU executing the reference-point setting program, the reference point where the first plane and the myocardium intersect each other is obtained. By the CPU executing the second-plane forming program, the second planes that extend in a direction orthogonal to the myocardium at the reference points are formed. By the CPU executing the image-generation-plane forming program, the first plane and the second planes are connected to form the image generation plane.

The computing part 8 is provided with a CPU and a storage (not shown) such as a ROM, a RAM and an HDD. A computing program for executing the function of the computing part is stored in the storage. A motion-information calculating program for executing the function of the motion-information calculator 81 and a color determining program for executing the function of the color determining part 82 are included in the computing program. By the CPU executing the motion-information calculating program, the wall motion information such as the strain and the strain rate of the myocardium in each cardiac phase is obtained. Moreover, by the CPU executing the color determining program, the colors according to the magnitude of the wall motion information are determined.

The display controller 9 is provided with a CPU and a storage (not shown) such as a ROM, a RAM and an HDD. A display controlling program for executing the function of the display controller 9 is stored in the storage. By the CPU executing the display controlling program, the display 11 displays the MPR image and the wall motion information.

Moreover, the controller 13 is provided with a CPU and a storage (not shown) such as a ROM, a RAM, and an HDD. A controlling program for executing the function of the controller 13 is stored in the storage. By the CPU executing the controlling program, the operation of each part of the ultrasonic imaging apparatus 1 is controlled.

The image processing program and the display controlling program of the present embodiment compose an example of an ultrasonic image processing program.

The image generation plane may be formed in each cardiac phase. Firstly, as described above, the first-plane forming part 74 forms the first plane 140 that passes through the designated point 130 on the reference axis 120 and is orthogonal to the reference axis 120.

As described above, the contour tracking part 71 obtains the position of each of the points composing the 3-dimensional contour of the endocardium and the position of each of the points composing the 3-dimensional contour of the epicardium in each cardiac phase.

The reference-point setting part 75 receives the coordinate information of the first plane 140 from the first-plane forming part 74 and obtains points where the contour of the myocardium and the first plane 140 intersect each other in each cardiac phase. For example, the reference-point setting part 75 obtains points where the contour of the endocardium 111 and the first plane 140 intersect each other in each cardiac phase and sets the intersecting points as the reference points.

That is, the reference-point setting part 75 obtains the positions of the reference points in each cardiac phase.

The second-plane forming part 76 receives the coordinate information of the reference points in each cardiac phase from the reference-point setting part 75 and obtains second planes that extend in a direction orthogonal to the contour of the endocardium 111 in each cardiac phase for each cardiac phase. That is, the second-plane forming part 76 forms second planes in each cardiac phase based on the endocardium 111 and the reference points in the same cardiac phase.

The image-generation-plane forming part 77 receives the coordinate information of the first plane from the first-plane forming part 74 and the coordinate information of the second planes in each cardiac phase from the second-plane forming part 76, and connects the first plane and the second planes in each cardiac phase at the reference points in each cardiac phase. The image-generation-plane forming part 77 forms an image generation plane in each cardiac phase through this connection.

The image-generation-plane forming part 77 then outputs the coordinate information of the image generation plane in each cardiac phase to the image generator 6. The image generator 6 generates MPR image data on the image generation plane in each cardiac phase, based on the volume data in each cardiac phase. That is, the image generator 6 generates MPR image data on the image generation plane in each cardiac phase, based on the volume data and the image generation plane in the same cardiac phase.

The display controller 9 then controls the display 11 to display an MPR image based on the MPR image data in each cardiac phase sequentially in each cardiac phase. In addition, the display controller 9 controls the display 11 to display in a state that a color assigned by the color determining part 82 is superimposed on each cardiac site of the myocardium on the MPR image in each cardiac phase. At this moment, the display controller 9 controls the display 11 to display in a state that the color assigned to each site of the myocardium on the image generation plane in the same cardiac phase is superimposed on the MPR image in each cardiac phase.

(Ultrasonic Image Processing Apparatus)

An ultrasonic image processing apparatus that generates MPR image data along the wall-thickness direction of the myocardium may be provided outside the ultrasonic imaging apparatus. This ultrasonic image processing apparatus comprises the abovementioned storage 5, image generator 6, image processor 7, computing part 8, display controller 9, user interface (UI) 10, and controller 13. The ultrasonic image processing apparatus acquires a plurality of volume data whose acquisition times are consecutive from the ultrasonic imaging apparatus, and generates MPR image data along the wall-thickness direction of the myocardium based on the plurality of volume data. In addition, the ultrasonic image processing apparatus obtains wall motion information by tracking the contour of the myocardium.

Volume data is acquired for each cardiac phase by scanning a heart with ultrasonic waves by using the ultrasonic imaging apparatus provided outside the ultrasonic image processing apparatus. Then, the ultrasonic image processing apparatus receives a plurality of volume data acquired by the ultrasonic imaging apparatus, and stores the plurality of volume data in the storage 5. The contour tracking part 71 of the ultrasonic image processing apparatus tracks the contour of the endocardium (epicardium) by obtaining the position of each of the points composing the 3-dimensional contour of the endocardium (epicardium) in each cardiac phase. The forming part 73 of the ultrasonic image processing apparatus obtains the second planes parallel to the wall-thickness direction of the myocardium, based on the position of each of the points composing the 3-dimensional contour.

Moreover, the computing part 8 of the ultrasonic image processing apparatus obtains wall motion information of the myocardium based on the position of each of the points composing the 3-dimensional contour and assigns a color according to the magnitude of the wall motion information to each site of the myocardium.

As described above, the ultrasonic image processing apparatus provided outside the ultrasonic imaging apparatus, similarly to the abovementioned ultrasonic imaging apparatus 1, also generates MPR image data on the plane toward the wall-thickness direction of the myocardium, in the myocardium. Consequently, it is possible to observe a cross-section of the myocardium along the wall-thickness direction. Additionally, since the orientation of the vector of the wall motion information and the wall-thickness direction of the myocardium represented in the MPR image coincide with each other, so it is possible to evaluate wall motion of the myocardium more properly.

(Operation)

Next, the operation of the ultrasonic imaging apparatus 1 (ultrasonic image processing apparatus) according to the embodiment of the present invention will be described with reference to FIG. 6. FIG. 6 is a flow chart for describing a series of operations of the ultrasonic imaging apparatus according to the embodiment of the present invention. In the present embodiment, a heart is a diagnosis site, and a plurality of volume data (moving image data) acquired at sequential times are acquired. Then, MPR image data on a plane along the wall-thickness direction of the myocardium is generated based on the volume data. Furthermore, wall-motion information used for evaluation of the cardiac function is obtained.

(Step S01)

First, the ultrasonic probe 2 is applied to the subject to transmit ultrasonic waves to the heart, and volume data in each cardiac phase (moving image data of the heart) is acquired. For example, ultrasonic waves are transmitted and received for one cardiac cycle or more, and volume data in each cardiac phase is thereby acquired for one cardiac cycle or more. The controller 13 receives ECG signals from outside the ultrasonic imaging apparatus 1, correlates each generated volume data and a time phase in which the volume data has been acquired, and controls the storage 5 to store them.

(Step S02)

The contour tracking part 71 reads out volume data from the storage 5, and executes pattern matching using a speckle pattern on two of the volume data. Through this pattern matching, the contour tracking part 71 obtains the position of each of the points composing the 3-dimensional contour of the myocardium in each cardiac phase. Then, the motion-information calculator 81 of the computing part 8 obtains wall-motion information such as the strain S(t) in the wall-thickness direction at each site of the myocardium, in each cardiac phase.

(Step S03)

On the other hand, the operator designates an arbitrary cardiac phase by using the operation part 12. Moreover, the operator designates an arbitrary cross-section for the volume data by using the operation part 12. Here, as an example, the operator designates a long-axis cross-section of the heart. Information indicating the cardiac phase designated by the operator and coordinate information of the long-axis cross-section are outputted from the user interface (UI) to the image generator 6 via the controller 13.

(Step S04)

The image generator 6 reads out the volume data correlated with the designated cardiac phase from the storage 5, and generates MPR image data (long-axis image data) in the long-axis cross-section of the heart based on the volume data. Then, the display controller 9 controls the display 11 to display a long-axis image based on the long-axis image data. For example, as shown in FIG. 2, the display controller 9 controls the display 11 to display the long-axis image 100 of the heart and the long-axis image 200 in a cross-section orthogonal to the long-axis image 100.

(Step S05)

Next, the operator designates the reference axis 120 that passes through the center of the long-axis image 100 along the long-axis direction of the long-axis image 100, by using the operation part 12, and further designates the arbitrary point 130 on the reference axis 120.

Coordinate information of the reference axis 120 and coordinate information of the point 130 on the long-axis image 100 are outputted from the user interface (UI) 10 to the controller 13. The controller 13 obtains coordinates of the reference axis 120 and coordinates of the point 130 in the 3-dimensional space based on the coordinate information in the 3-dimensional space of the long-axis cross-section of the long-axis image 100, and outputs the coordinate information to the forming part 73.

(Step S06)

The first-plane forming part 74 receives the coordinate information of each of the points composing the contour of the myocardium in the cardiac phase designated by the operator, from the contour tracking part 71, and sets the reference axis 120 and the point 130 for contour of the myocardium. Then, as shown in FIG. 4, the first-plane forming part 74 forms the first plane 140 passing through the point 130 and being orthogonal to the reference axis 120. Then, the first-plane forming part 74 outputs coordinate information in the 3-dimensional space of the formed first plane 140, to the reference-point setting part 75.

(Step S07)

The reference-point setting part 75 sets a reference point where the contour of the endocardium 111 and the first plane 140 intersect each other, as shown in FIG. 4, for example. At this moment, the reference-point setting part 75 obtains a plurality of reference points 150A . . . 150N . . . intersecting the contour of the endocardium 111 in a 360-degree periphery within the first plane 140. Then, the second-plane forming part 76 forms the second planes 160A . . . 160N . . . extending in a direction orthogonal to the contour of the endocardium 111, for the respective reference points 150A . . . 150N . . . obtained in the 360-degree periphery within the first plane 140, as shown in FIGS. 3 and 4, for example. The second planes are orthogonal to the contour of the endocardium 111, and therefore, are parallel to the wall-thickness direction of the myocardium 110.

(Step S08)

Next, the image-generation-plane forming part 77 connects the first plane 140 formed inside the endocardium 111 (in the cardiac cavity) with the second planes 160A . . . 160N . . . formed outside the endocardium 111 at the respective reference points 150A . . . 150N . . . as shown in FIG. 4, for example, thereby forming one image generation plane.

(Step S09)

The image generator 6 reads out the volume data acquired in the designated cardiac phase from the storage 5. Then, the image generator 6 executes the MPR process on the read-out volume data, thereby generating MPR image data on the image generation plane. Thus, the MPR image data on the image generation plane composed of the first plane 140 and the second planes 160A . . . 160N . . . is generated. Then, the image generator 6 outputs the MPR image data on the image generation plane to the display controller 9.

(Step S10)

On the other hand, the color determining part 82 determines a color according to the magnitude of the wall motion information such as the strain S(t) at each site on the image generation plane, and assigns the color to each site. The color determining part 82 then outputs coordinate information of each site on the image generation plane and information indicating the color assigned to the site (color information), to the display controller 9. The display controller 9 then controls the display 11 to display in a state where the color assigned to each site of the myocardium by the color determining part 82 is superimposed on an MPR image generated by the image generator 6.

For example, as shown in FIG. 2, the display controller 9 controls the display 11 to display the short-axis image 300 of the image generation plane formed by the first plane 140 passing through point 130 on the reference axis 120 and the second planes 160A . . . 160N . . . orthogonal to the myocardium. The display controller 9 then controls the display 11 to display by superimposing the color according to the magnitude of the wall motion information at each site on the image generation plane on each site of the short-axis image 300.

As described above, according to the present embodiment, in the myocardium 110, the second planes orthogonal to the myocardium 110 are obtained and MPR image data (short-axis image data) on the second planes are generated, so that it is possible to generate the MPR image data along the wall-thickness direction of the myocardium.

Consequently, it is possible to observe a cross-section along the wall-thickness direction of the myocardium 110. Furthermore, the direction of the vector of the wall motion information and the wall-thickness direction of the myocardium represented in the short-axis image are equal, so that the actual wall motion information in the short-axis image is displayed in the short-axis image.

Consequently, it is possible to more appropriately evaluate the wall motion at each site of the myocardium.

First Modification

Figure 8A:
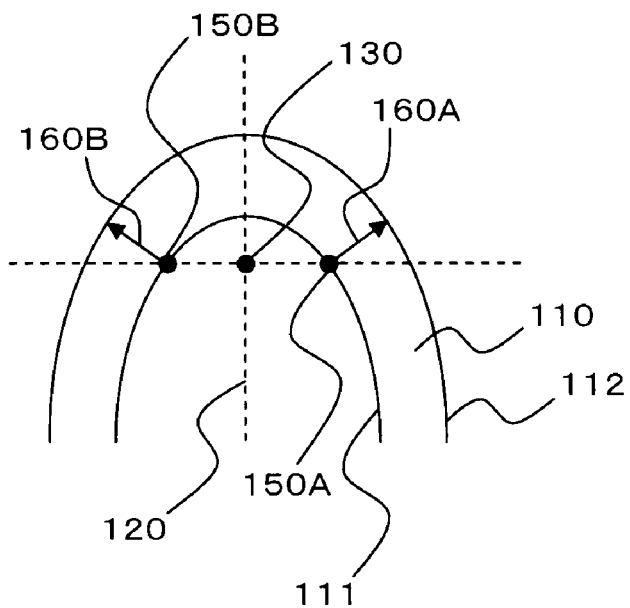
FIG. 8A is a schematic view illustrating the contour of a myocardium in a cross-section along the long-axis direction of the myocardium.
Figure 8B:
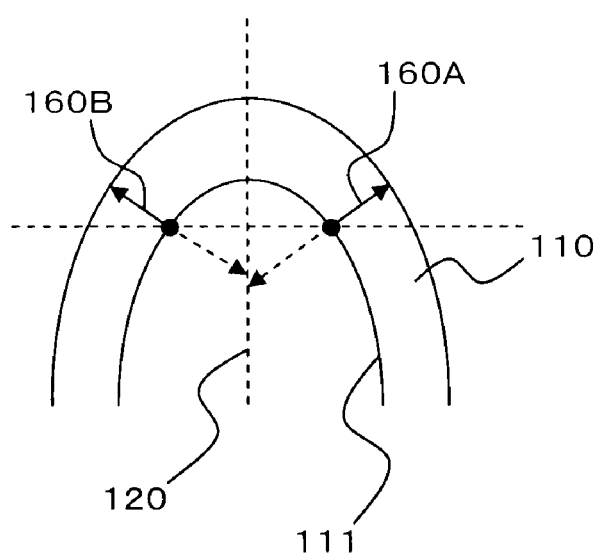
FIG. 8B is a schematic view illustrating the contour of a myocardium in a cross-section along the long-axis direction of the myocardium.

Next, a first modification of the ultrasonic imaging apparatus according to the abovementioned embodiment will be described with reference to FIGS. 7, 8A and 8B. FIG. 7 is a view of a screen illustrating an example of an image displayed on the display in the first modification. FIGS. 8A and 8B are schematic views illustrating the contour of the myocardium on a cross-section along the long-axis direction of the myocardium.

In the first modification, the image-generation-plane forming part 77 forms an image generation plane by executing a different process from that in the abovementioned embodiment. Each part other than the image-generation-plane forming part 77 executes the same process as in the abovementioned embodiment.

Similarly in the abovementioned embodiment, the image generator 6 reads out volume data correlated with the cardiac phase designated by the operator from the storage 5, and generates long-axis image data of a long-axis cross-section of the heart, based on the volume data. The display controller 9 then, as shown in FIG. 7, controls the display 11 to display the long-axis image 100 of the heart. The display controller 9 may control the display 11 to display the long-axis image 200, which is a cross-section orthogonal to the long-axis image 100.

The operator then designates the reference axis 120 by using the operation part 12, and further designates the arbitrary point 130 on the reference axis 120. The controller 13 outputs coordinate information of the reference axis 120 and coordinate information of the point 130 in the 3-dimensional space to the forming part 73.

The first-plane forming part 74, similarly in the abovementioned embodiment, forms a first plane orthogonal to the reference axis 120 through the point 130 designated by the operator.

The reference-point setting part 75 then, similarly in the abovementioned embodiment, obtains reference points where the contour of the myocardium and the first plane intersect each other. At this moment, the reference-point setting part 75 obtains the reference points orthogonal to the contour of the endocardium 111 in a 360-degree periphery within the first plane. For example, as shown in FIG. 8A, the reference-point setting part 75 obtains a plurality of reference points 150A, 150B ... where the contour of the endocardium 111 and the first plane intersect each other. The reference-point setting part 75 may obtain points where the first plane and, instead of the contour of the endocardium 111, the contour of the epicardium 112 intersect each other and set the points as a reference points.

The second-plane forming part 76, similarly in the abovementioned embodiment, forms second planes that extend in a direction orthogonal to the contour of the endocardium 111 within the long-axis cross-section, with reference to the reference points set by the reference-point setting part 75. For example, as shown in FIG. 8A, the second-plane forming part 76 forms second plane 160A that extends in a direction orthogonal to the contour of the endocardium 111 within the long-axis cross-section with reference to the reference point 150A.

The second-plane forming part 76 then forms second planes 160A, 160B ... that extend in a direction orthogonal to the contour of the endocardium 111, at the reference points 150A, 150B ... obtained in a 360-degree periphery within the first plane. The second planes are orthogonal to the contour of the endocardium 111, and therefore, are parallel to the wall-thickness direction of the myocardium 110.

The image-generation-plane forming part 77 then receives the coordinate information of the second planes from the second-plane forming part 76, and extends the second planes to the reference axis 120. For example, as shown in FIG. 8B, the image-generation-plane forming part 77 extends the second plane 160A to the reference axis 120, and extends the second plane 160B to the reference axis 120. The image-generation-plane forming part 77 then forms one image generation plane by connecting the surfaces formed by extending the second planes 160A, 160B ... to the reference axis 120. Consequently, the image generation plane comprises the second plane 160A, 160 ... not only in the outside of the endocardium 111 but also the inside (in the cardiac cavity).

The image generator 6 reads out the volume data acquired in the cardiac phase designated by the operator from the storage 5. The image generator 6 then executes the MPR process on the read-out volume data, thereby generating MPR image data of the image generation plane formed by the image-generation-plane forming part 77. Consequently, the MPR image data on the image generation plane composed of the second planes 160A, 160B ... is generated. The display controller 9 then controls the display 11 to display an MPR image based on the MPR image data of the image generation plane.

Moreover, the image generator 6 reads out the volume data acquired in each cardiac phase from the storage 5 and executes the MPR process on the volume data acquired in each cardiac phase, thereby generating the MPR image data of the image generation plane formed by the image-generation-plane forming part 77, in each cardiac phase. Subsequently, upon receiving the MPR image data in each cardiac phase from the image generator 6, the display controller 9 controls the display 11 to display the MPR image in each cardiac phase sequentially for each cardiac phase.

As described above, according to the ultrasonic imaging apparatus according to the first modification, for the myocardium 110, the second planes 160A, etc., orthogonal to the myocardium 110 are obtained and MPR image data on the second planes 160A, etc., are generated. Therefore, it is possible to observe a cross-section of the myocardium 110 along the wall-thickness direction. In addition, in the first modification, the second planes 160A, etc., are extended to the reference axis 120, so that there is no gap at the border between the myocardium 110 and the cardiac cavity. Thus, it is possible to generate a smooth image at the border. To be more precise, there is no gap in the image, at the reference points 150A, 150B ... where the endocardium 111 and the first plane intersect each other, and a smooth image is obtained around the reference points 150A, etc. Moreover, since it is possible to obtain short-axis image data along the wall-thickness direction only by the operator's designation of an arbitrary point on the long-axis image, it is possible to observe a cross-section with a desired wall thickness by a simple operation.

Similarly in the abovementioned embodiment, the computing part 8 obtains wall motion information of the myocardium and assigns a color according to the magnitude of the wall motion information to each site of the myocardium. In the first modification, the color determining part 82 determines a color according to the magnitude of the wall motion information at each site on the image generation plane formed by the image-generation-plane forming part 77. For example, the color determining part 82 determines a color according to the magnitude of the strain S(t) at each site on the image generation plane, and assigns the color to each site.

The display controller 9 then controls the display 11 to display the color assigned by the color determining part 82 in a superimposed manner on each site of the myocardium, on the MPR image generated by the image generator 6.

For example, as shown in FIG. 7, the display controller 9 controls the display 11 to display a short-axis image 400 of the image generation plane composed of the second planes 160A, 160B ... formed by designating the point 130 on the reference axis 120. The display controller 9 then controls the display 11 to display a color according to the magnitude of the wall motion information at each site on the image generation plane in a superimposed state on each site of the short-axis image 400. Moreover, when the operator designates other points 131 and 132 on the reference axis 120 by using the operation part 12, the forming part 73 forms an image generation plane corresponding to each of the points. Then, the image generator 6 generates short-axis image data of the image generation plane corresponding to the point 131, and generates short-axis image data of the image generation plane corresponding to the point 132. The computing part 8 determines a color according to the magnitude of the wall motion information at each site on each of the image generation planes. Then, the display controller 9 controls the display 11 to display a short-axis image 410 of the image generation plane corresponding to the point 131 and a short-axis image 420 of the image generation plane corresponding to the point 132. Furthermore, the display controller 9 controls the display 11 to display the color according to the magnitude of the wall motion information in a superimposed state on each of the short-axis image 410 and the short-axis image 420.

As described above, according to the ultrasonic imaging apparatus according to the first modification, similarly in the abovementioned embodiment, the direction of the vector of the wall motion information coincides with the wall-thickness direction of the myocardium represented in the short-axis image. Consequently, in the short-axis image, the actual wall motion information of the short-axis image is displayed, whereby it is possible to more properly evaluate the wall motion at each site of the myocardium.

Moreover, similarly in the abovementioned embodiment, the process in the first modification may be executed by the ultrasonic image processing apparatus provided outside the ultrasonic imaging apparatus.

Moreover, similarly in the abovementioned embodiment, the image generation plane may be formed for each cardiac phase. Firstly, the first-plane forming part 74 forms the first plane orthogonal to the reference axis 120 through the point 130 designated on the reference axis 120. The contour tracking part 71, as described above, obtains the position of each of the points composing the 3-dimensional contour of the endocardium and the position of each of the points composing the 3-dimensional contour of the epicardium in each cardiac phase.

The reference-point setting part 75 receives the coordinate information of the first plane from the first-plane forming part 74, and obtains points where the contour of the myocardium and the first plane intersect each other in each cardiac phase. That is, the reference-point setting part 75 obtains the positions of the reference points in each cardiac phase.

The second-plane forming part 76 receives the coordinate information of the reference points in each cardiac phase from the reference-point setting part 75, and obtains second planes that extend in a direction orthogonal to the contour of the endocardium 111 in each cardiac phase, for each cardiac phase. That is, the second-plane forming part 76 forms the second planes in each cardiac phase, based on the endocardium 111 and the reference point in the same cardiac phase.

The image-generation-plane forming part 77 receives the coordinate information of the second planes in each cardiac phase from the second-plane forming part 76, and extends the second planes to the reference axis 120. Then, the image-generation-plane forming part 77 forms one image generation plane for each cardiac phase, by connecting the second planes in the same cardiac phase. Then, the image-generation-plane forming part 77 outputs coordinate information of the image generation plane in each cardiac phase to the image generator 6.

The image generator 6 generates MPR image data of the image generation plane in each cardiac phase based on the volume data and the image generation plane in the same cardiac phase. The display controller 9 controls the display 11 to sequentially display MPR images based on the MPR image data in each cardiac phase. In addition, the display controller 9 controls the display 11 to display by superimposing a color assigned by the color determining part 82 on each site of the myocardium on the MPR image in each cardiac phase.

At this moment, the display controller 9 controls the display 11 to display by superimposing the color assigned on the image generation plane in the same cardiac phase, on each site of the myocardium on the MPR image in each cardiac phase.

(Operation)

Figure 9:
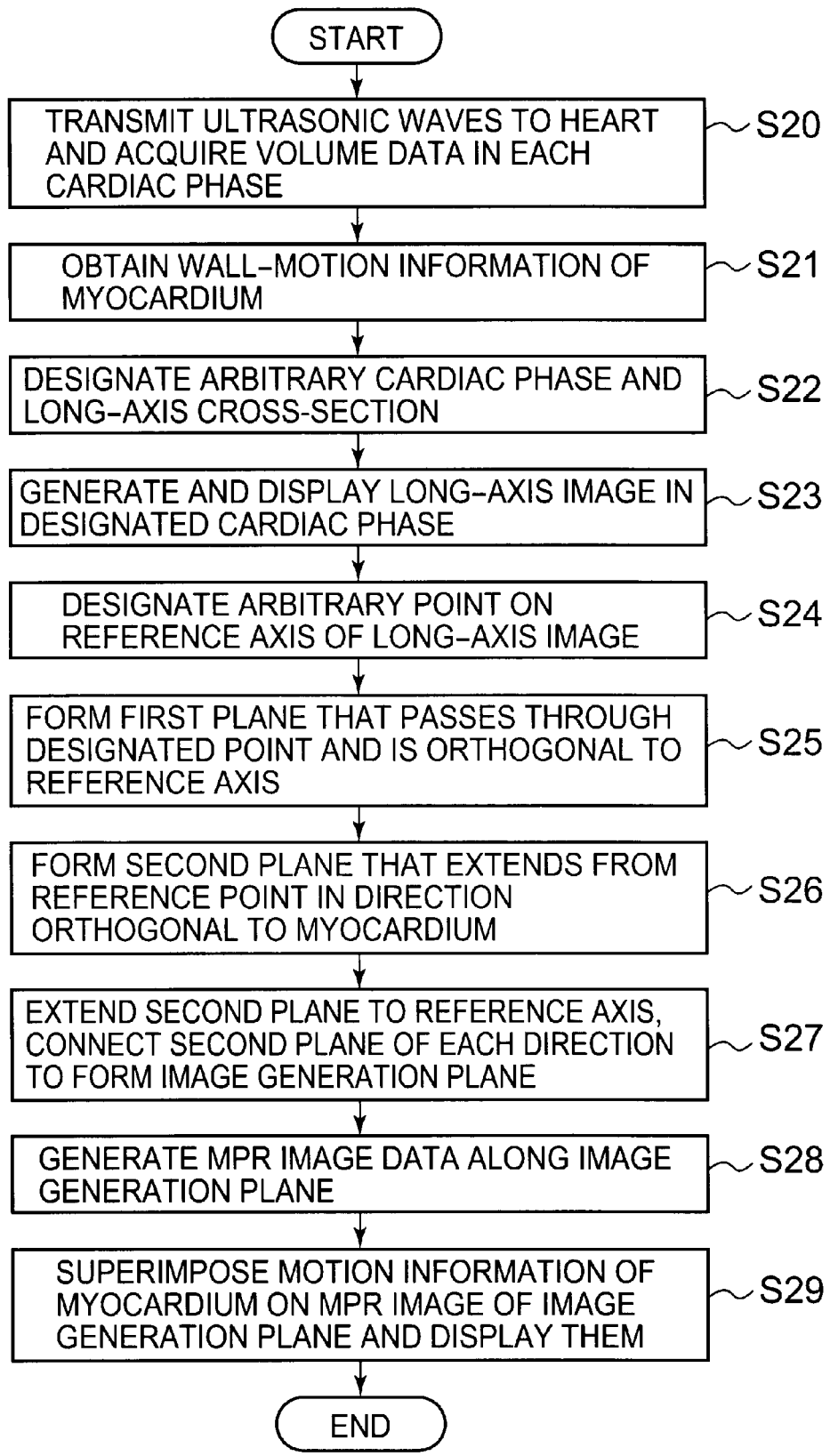
FIG. 9 is a flow chart for describing a series of operations of the ultrasonic imaging apparatus according to the first modification.

Next, the operation of the ultrasonic imaging apparatus (ultrasonic image processing apparatus) according to the first modification will be described with reference to FIG. 9. FIG. 9 is a flow chart for describing a series of actions of the ultrasonic imaging apparatus according to the first modification.

(Step S20)

First, the ultrasonic probe 2 is applied to the subject to transmit ultrasonic waves to the heart, and volume data (moving image data) in each cardiac phase is acquired.

(Step S21)

The contour tracking part 71 reads out volume data from the storage 5, and executes pattern matching by using a speckle pattern on two of the volume data. Through this pattern matching, the contour tracking part 71 obtains the position of each of the points composing a 3-dimensional contour of the myocardium in each cardiac phase. The motion-information calculator 81 obtains wall motion information at each site of the myocardium for each cardiac phase.

(Step S22)

On the other hand, the operator designates an arbitrary cardiac phase and a long-axis cross-section of the heart by using the operation part 12.

(Step S23)

The image generator 6 reads out the volume data related with the designated cardiac phase from the storage 5, and generates MPR image data in the long-axis cross-section of the heart (long-axis image data), based on the volume data. As shown in FIG. 7, the display controller 9 controls the display 11 to display the long-axis image 100 of the heart and the long-axis image 200 in a cross-section orthogonal to the long-axis image 100.

(Step S24)

The operator designates the reference axis 120 by using the operation part 12, and further designates the arbitrary point 130 on the reference axis 120. The controller 13 outputs coordinate information of the reference axis 120 and coordinate information of the point 130 in the 3-dimensional space to the forming part 73.

(Step S25)

The first-plane forming part 74, as shown in FIG. 8A, forms a first plane orthogonal to the reference axis 120 through point 130.

(Step S26)

The reference-point setting part 75, as shown in FIG. 8A, obtains reference points where the contour of the endocardium 111 and the first plane intersect each other. At this moment, the reference-point setting part 75 obtains a plurality of reference points 150A, 150B . . . intersecting the contour of the endocardium 111 in a 360-degree periphery within the first plane. The second-plane forming part 76 forms second planes 160A, 160B . . . extending in a direction orthogonal to the contour of the endocardium 111, at the respective reference points 150A, 150B . . . obtained in a 360-degree periphery within the first plane.

(Step S27)

The image-generation-plane forming part 77, as shown in FIG. 8B, extends the respective second planes 160A, 160B . . . to the reference axis 120, and connects the second planes of the respective directions, thereby forming one image generation plane.

(Step S28)

The image generator 6 reads out the volume data acquired in the designated cardiac phase from the storage 5, and executes the MPR process on the volume data, thereby generating MPR image data on the image generation plane. Consequently, the MPR image data on the image generation plane composed of the second planes 160A, 160B . . . is generated.

(Step S29)

On the other hand, the color determining part 82 determines a color according to the magnitude of wall motion information at each site on the image generation plane, and assigns the color to each site.

The display controller 9 controls the display 11 to display the MPR image generated by the image generator 6 with the color assigned by the color determining part 82 superimposed on each site of the myocardium. For example, as shown in FIG. 7, the display controller 9 controls the display 11 to display the short-axis image 400 on the image generation plane composed of the second planes 160A, 160B . . . formed by designating the point 130. The display controller 9 then controls the display 11 to display while superimposing the color according to the magnitude of the wall motion information at each site on the image generation plane, on each site of the short-axis image 400.

Second Modification

Figure 10A:
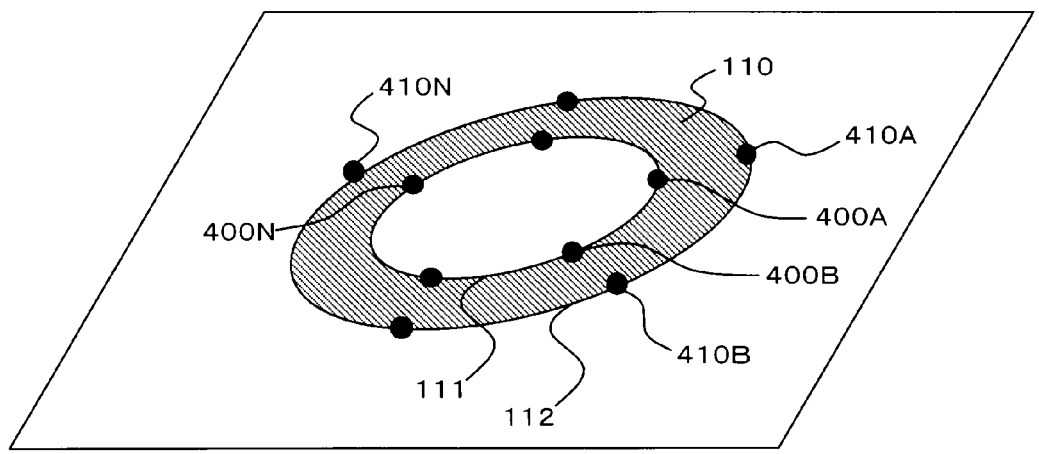
FIG. 10A is a schematic view illustrating the contour of a myocardium in a cross-section along the short-axis direction of the myocardium.
Figure 10B:
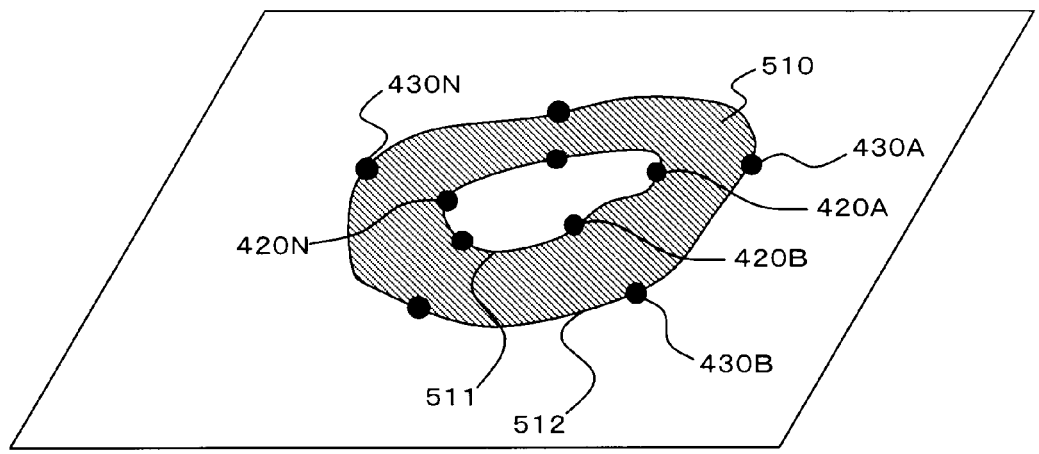
FIG. 10B is a schematic view illustrating the contour of a myocardium in a cross-section along the short-axis direction of the myocardium.

Next, a second modification of the ultrasonic imaging apparatus 1 according to the abovementioned embodiment will be described with reference to FIG. 10A and FIG. 10B. FIG. 10A and FIG. 10B are schematic views illustrating the contour of the myocardium in a cross-section along the short-axis direction of the myocardium.

In this modification 2, the second-plane forming part 76 executes a process different from that in the above-mentioned embodiment, thereby forming second planes orthogonal to the myocardium.

First, the operator designates an arbitrary cardiac phase by using the operation part 12. The cardiac phase designated by the operator is set as the initial time phase. Further, the operator designates an arbitrary cross-section for the volume data by using the operation part 12. In this second modification, the operator designates a short-axis cross-section of the heart. Information showing the initial time phase designated by the operator and coordinate information of the short-axis cross-section are outputted from the user interface (UI) 10 to the contour tracking part 71 via the controller 13.

When receiving the information showing the initial time phase and the coordinate information of the short-axis cross-section from the controller 13, the contour tracking part 71 sets tracking points on the contour of the myocardium in the short-axis cross-section in the initial time phase. For example, as shown in FIG. 10A, the contour tracking part 71 sets tracking points 400A, 400B . . . 400N . . . on the contour of the endocardium 111 of the myocardium 110 in the initial time phase.

That is, the contour tracking part 71 sets the tracking points 400A, etc., on the contour of the endocardium 111 in a 360-degree periphery in the designated short-axis cross-section. These tracking points 400A, etc., are set in the same short-axis cross-section. The contour tracking part 71 may set tracking points 410A, 410B . . . 410N on the contour of the epicardium 112 of the myocardium 110 in the initial time phase. The tracking points 410A, etc. set for the epicardium 112 are set also in the same short-axis cross-section.

The contour tracking part 71 executes pattern matching using a speckle pattern on two of the volume data, thereby obtaining the positions of the set tracking points for each cardiac phase.

Consequently, the positions of the tracking points are tracked for each cardiac phase. For example, the contour tracking part 71 obtains the positions of the tracking points 400A, etc. set on the contour of the endocardium 111, for each cardiac phase. The contour tracking part 71 may obtain the positions of the tracking point 410A, etc. set on the contour of the epicardium 112, for each cardiac phase.

Here, the positions of the tracking points 400A, etc. in an arbitrary cardiac phase will be shown in FIG. 10B. In FIG. 10B, a myocardium 510 corresponds to the myocardium 110 in the initial time phase. Moreover, the contour of an endocardium 511 corresponds to the contour of the endocardium 111 in the initial time phase. In addition, the contour of an epicardium 512 corresponds to the contour of the epicardium 112 in the initial time phase. Moreover, tracking points 420A, 420B . . . 420N correspond to the tracking points 400A, 400B . . . 400N . . . set in the initial time phase. In addition, tracking points 430A, 430B . . . 430N . . . correspond to the tracking points 410A, 410B . . . 410N . . . set in the initial time phase.

The tracking points 400A, etc. set within the same short-axis cross-section in the initial time phase do not exist within the same short-axis cross-section in the arbitrary cardiac phase after tracking.

This is because the heart moves not only in the wall-thickness direction of the myocardium but also in the long-axis direction of the heart when the heart contracts and dilates. In the second modification, regarding the tracking points set in the initial time phase, the positions in the arbitrary cardiac phase are obtained, and short-axis image data in a cross-section parallel to the wall-thickness direction of the myocardium is generated based on the positions of the tracking points in the arbitrary cardiac phase.

The contour tracking part 71 outputs coordinate information of the respective tracking points in each cardiac phase to the forming part 73.

The second-plane forming part 76 forms second planes extending in a direction orthogonal to the contour of the endocardium, within the long-axis cross-section, with reference to the tracking points in the arbitrary cardiac phase. For example, as shown in FIG. 10B, the second-plane forming part 76 forms a second plane extending in a direction orthogonal to the contour of the endocardium 511 for each of the tracking points, within the long-axis cross-section, with reference to each of the tracking points 420A, 420B . . . 420N . . . on the contour of the endocardium 511 in a certain cardiac phase. The second planes are orthogonal to the contour of the endocardium 511 in the certain cardiac phase, and therefore, are parallel to the wall-thickness direction of the myocardium 510 in the cardiac phase. The second-plane forming part 76 then forms the second planes in each cardiac phase, with reference to each of the tracking points in each cardiac phase. The second-plane forming part 76 outputs coordinate information of the second planes in each cardiac phase to the image-generation-plane forming part 77.

For example, similarly in the modification 1, the image-generation-plane forming part 77 extends each of the second planes in a certain cardiac phase to the central axis of the myocardium, and connects the second planes, thereby forming an image generation plane in the cardiac phase. Alternatively, the image-generation-plane forming part 77 may obtain a plane orthogonal to the central axis of the myocardium through the tracking points in a cardiac phase, and connect each of the second planes to the orthogonal plane, thereby forming an image generation plane in the cardiac phase. The image-generation-plane forming part 77 then forms an image generation plane in each cardiac phase, based on the second planes formed for each cardiac phase.

The image generator 6 reads out volume data acquired in an arbitrary cardiac phase from the storage 5. Then, the image generator 6 executes the MPR process on the read-out volume data, thereby generating MPR image data (short-axis image data) on the image generation plane in the same cardiac phase formed by the image-generation-plane forming part 77.

Then, the image generator 6 executes the MPR process on the volume data in each cardiac phase, thereby generating short-axis image data of the image generation plane in each cardiac phase. The display controller 9 controls the display 11 to sequentially display a short-axis image based on the short-axis image data in each of the cardiac phases, in accordance with the order of the cardiac phases.

As described above, the ultrasonic imaging apparatus according to the second modification tracks, for each cardiac phase, the positions of the tracking points set in the initial time phase, obtains second planes orthogonal to the myocardium in an arbitrary cardiac phase, and generates the MPR image data of the second planes. Therefore, it is possible to observe a cross-section along the wall-thickness direction of the myocardium in an arbitrary cardiac phase. Thus, it is possible to cause the display 11 to display a short-axis image in each of the cardiac phases in accordance with the order of the cardiac phases, thereby consecutively observe the shape of the cross-section along the wall-thickness direction in each of the cardiac phases.

Similarly in the abovementioned embodiment, the computing part 8 obtains wall motion information of the myocardium, and assigns a color according to the magnitude of the wall motion information at each site of the myocardium. In the second modification, the color determining part 82 determines a color corresponding to the magnitude of the wall motion information at each site on the image generation plane in each cardiac phase, and assigns the color to each site on the image generation plane in each cardiac phase.

The display controller 9 controls the display 11 to display in a manner that the color assigned on the image generation plane in the same cardiac phase is superimposed on each site of the myocardium on the short-axis image in the arbitrary cardiac phase generated by the image generator 6. Then, the display controller 9 controls the display 11 to display the short-axis image in each of the cardiac phases in accordance with the order of the cardiac phases, and further controls the display 11 to display in a manner that the color assigned on the image generation plane in each cardiac phase is superimposed on the short-axis image in the same cardiac phase.

As described above, according to the ultrasonic imaging apparatus according to this second modification, the direction of the vector of the wall motion information in each cardiac phase coincides with the wall-thickness direction of the myocardium represented in the short-axis image in each cardiac phase. Consequently, actual wall motion information of the short-axis image in each cardiac phase is displayed in the short-axis image in each cardiac phase, and it becomes possible to evaluate the wall motion at each part of the myocardium more properly for each cardiac phase. Then, by causing the display 11 to display the short-axis image and the wall motion information in each of the cardiac phases in accordance with the order of the cardiac phases, it becomes possible to consecutively observe the shape of a cross-section along the wall-thickness direction in each of the cardiac phases and the wall motion information in the cross-section.

Moreover, as in the aforementioned embodiment, the process in the second modification may be executed by an ultrasonic image processing apparatus provided outside the ultrasonic imaging apparatus.

(Operation)

Figure 11:
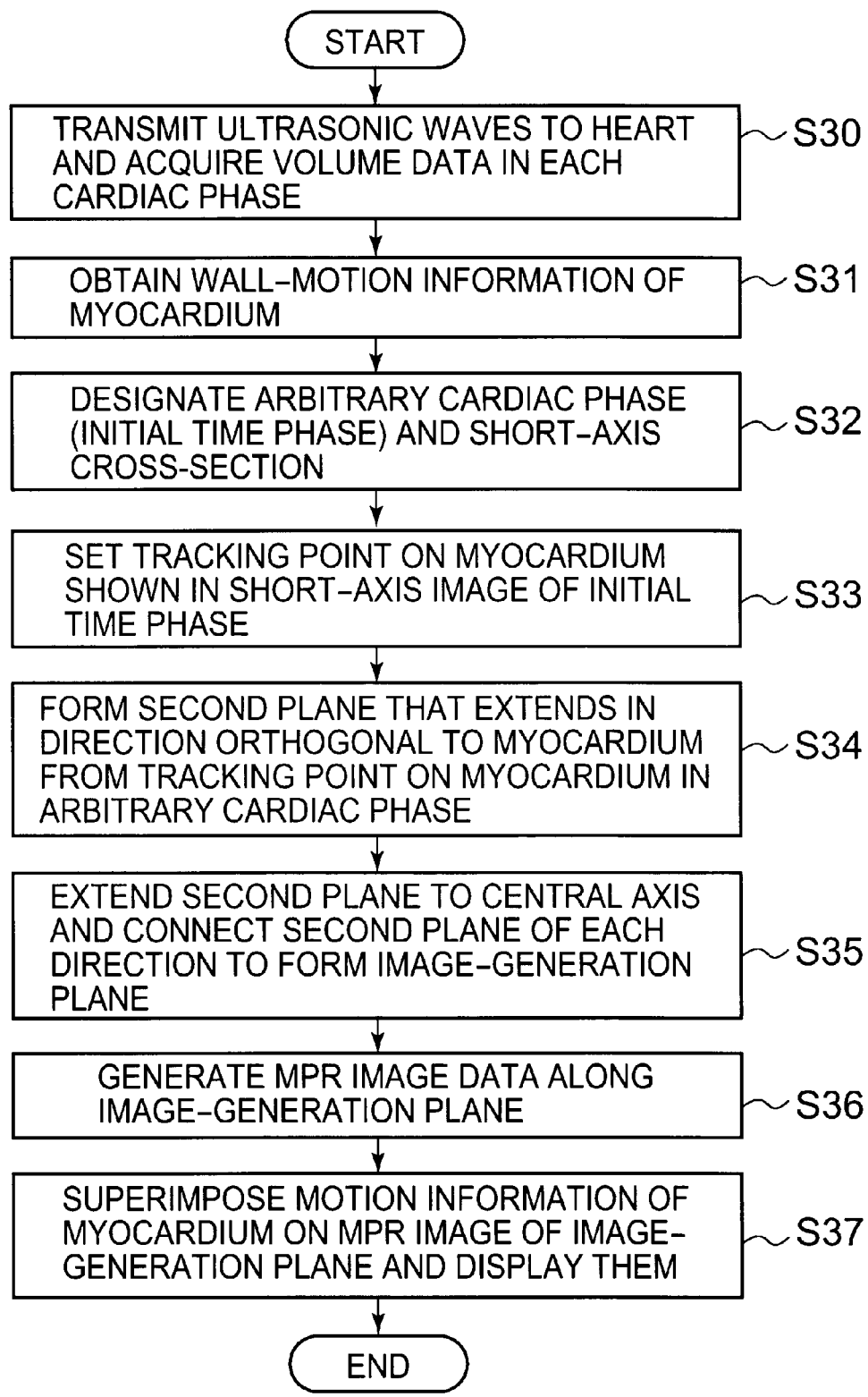
FIG. 11 is a flow chart for describing a series of operations of an ultrasonic imaging apparatus according to a second modification.

Next, the Operation of the Ultrasonic Imaging Apparatus (ultrasonic image processing apparatus) according to the second modification will be described with reference to FIG. 11. FIG. 11 is a flow chart for describing a series of operations of the ultrasonic imaging apparatus according to the second modification.

(Step S30)

The ultrasonic probe 2 is applied to a subject to transmit ultrasonic waves to the heart of the subject, and volume data (moving image data) in each cardiac phase is acquired.

(Step S31)

The contour tracking part 71 reads out the volume data from the storage 5, and executes pattern matching using a speckle pattern on two of the volume data. Through this pattern matching, the contour tracking part 71 obtains the position of each of the points composing a 3-dimensional contour of the myocardium in each cardiac phase. The motion-information calculator 81 then obtains wall motion information at each site of the myocardium, for each cardiac phase.

(Step S32)

On the other hand, the operator designates an arbitrary cardiac phase (initial time phase) and a short-axis cross-section of the heart by using the operation part 12.

(Step S33)

The contour tracking part 71, for example, as shown in FIG. 10A, sets tracking points 400A, 400B . . . 400N . . . on the contour of the endocardium 111 within the designated short-axis cross-section in the initial time phase. Specifically, the contour tracking part 71 sets the tracking points 400A, etc., on the contour of the endocardium 111 in a 360-degree periphery within the designated short-axis cross-section.

(Step S34)

Then, the contour tracking part 71 executes pattern matching using a speckle pattern on two of the volume data, thereby obtaining the positions of the set tracking point 400A, etc. for each cardiac phase.

For example, as shown in FIG. 10B, the contour tracking part 71 obtains the positions of tracking points 420A, etc. in a certain cardiac phase. The second-plane forming part 76 then forms second planes that extend in a direction orthogonal to the contour of the endocardium, within a long-axis cross-section, with reference to the tracking points in the arbitrary cardiac phase. For example, as shown in FIG. 10B, the second-plane forming part 76 forms the second planes that extend in a direction orthogonal to the contour of an endocardium 511 within the long-axis cross-section, with reference to each of the tracking points 420A 420B . . . 420N . . . on the contour of the endocardium 511 in the cardiac phase as a reference. The second-plane forming part 76 then forms the second planes in each cardiac phase with reference to each tracking point in each cardiac phase.

(Step S35)

The image-generation-plane forming part 77 extends each second plane in the cardiac phase to the central axis of the myocardium and connects the respective second planes, thereby forming an image generation plane in the cardiac phase.

(Step S36)

The image generator 6 then generates MPR image data (short-axis image data) of the image generation plane in an arbitrary cardiac phase by executing the MPR process on the volume data acquired in the cardiac phase. The image generator 6 generates short-axis image data of the image generation plane in each cardiac phase by MPR processing of the volume data in each cardiac phase.

(Step S37)

On the other hand, the color determining part 82 determines a color according to the size of wall motion information at each site on the image generation plane in each cardiac phase and assigns the color to each site on the image generation plane in each cardiac phase. The display controller 9 then controls the display 11 to display the color assigned on the image generation plane in the same cardiac phase in an overlapping manner at each site of the myocardium in the short-axis image in the arbitrary cardiac phase generated by the image generator 6.

The display controller 9 then controls the display 11 to display the color assigned to each site on the image generation plane in the same cardiac phase in an overlapping manner in the short-axis image based on the short-axis image data in each cardiac phase according to the order of the cardiac phases.

What is claimed is:

1. An ultrasonic image processing apparatus, comprising:
    a contour specifying part configured to receive volume data representing a subject acquired by transmission of ultrasonic waves to the subject and specify a 3-dimensional contour of a myocardium based on the volume data;
    a forming part configured to set a reference point on the contour of the myocardium and form an image generation plane including a plane substantially orthogonal to the contour of the myocardium at the reference point;
    an image generator configured to generate image data on the image generation plane based on the volume data; and
    a display controller configured to control a display to display an image based on the image data.

2. The ultrasonic image processing apparatus according to claim 1, wherein:
    the forming part sets a first plane intersecting the contour of the myocardium, obtains a point where the first plane intersects the contour of the myocardium, sets the point as the reference point, and forms the image generation plane including a second plane substantially orthogonal to the myocardium at the reference point; and
    the image generator generates image data on the image generation plane including the second plane based on the volume data.

3. The ultrasonic image processing apparatus according to claim 2, wherein:
    the forming part sets a reference axis piercing the contour of the myocardium, receives a designation of an arbitrary point on the reference axis, obtains a point where the first plane passing through the designated point intersects the contour of the myocardium, sets the point as the reference point, and forms the image generation plane including the second plane substantially orthogonal to the myocardium at the reference point.

4. The ultrasonic image processing apparatus according to claim 3, wherein:
    the image generator generates long-axis image data in a cross-section along a long-axis direction of a heart based on the volume data;
    the display controller controls the display to display a long-axis image based on the long-axis image data;
    the forming part sets the reference axis piercing the long-axis image along the long-axis direction, receives the designation of the arbitrary point on the reference axis, obtains a point where the first plane passing through the designated point and substantially orthogonal to the reference axis intersects the contour of the myocardium, sets the point as the reference point, and forms the image generation plane including the second plane substantially orthogonal to the myocardium at the reference point;
    the image generator further generates short-axis image data on the image generation plane including the second plane based on the volume data; and
    the display controller further controls the display to display a short-axis image based on the short-axis image data.

5. The ultrasonic image processing apparatus according to claim 2, wherein:
    the forming part connects the first plane with the second plane at the reference point, thereby forming the image generation plane; and
    the image generator generates image data on the image generation plane formed by connecting the first plane with the second plane, based on the volume data.

6. The ultrasonic image processing apparatus according to claim 2, wherein:
    the forming part extends the second plane to the reference axis, thereby forming the image generation plane; and
    the image generator generates image data on the image generation plane formed by extending the second plane to the reference axis, based on the volume data.

7. The ultrasonic image processing apparatus according to claim 2, wherein:
    the forming part obtains a point where the first plane intersects the contour of an endocardium or epicardium of the myocardium specified by the contour specifying part, and sets the point as the reference point.

8. The ultrasonic image processing apparatus according to claim 1, further comprising:
    a storage configured to store the volume data acquired for each time phase by transmission of ultrasonic waves to the subject; and
    a computing part, wherein:
    the contour specifying part obtains a position of each of points composing the 3-dimensional contour of the myocardium in the volume data acquired in each time phase, for each time phase, by pattern matching;
    the computing part obtains motion information indicating a motion state of the myocardium in the each time phase, based on the position of each of the points composing the contour in the each time phase;
    the forming part sets a reference point on the contour of the myocardium in an arbitrary time phase, and forms the image generation plane for the myocardium in the arbitrary time phase;
    the image generator generates image data on the image generation plane in the arbitrary time phase, based on volume data acquired in the arbitrary time phase; and
    the display controller controls the display to display in a state where motion information indicating a motion state on the image generation plane in the arbitrary time phase is superimposed on an image based on the image data in the arbitrary time phase.

9. The ultrasonic image processing apparatus according to claim 1, further comprising:

a storage configured to store the volume data acquired for each time phase by transmission of ultrasonic waves to the subject, wherein:

the contour specifying part obtains a position of each of points composing the 3-dimensional contour of the myocardium in the volume data acquired in each time phase, for each time phase, by pattern matching;

the forming part receives a designation of an arbitrary plane intersecting volume data acquired in a specified time phase, obtains a point where the arbitrary plane intersects the contour of the myocardium, sets a position of the intersecting point in an arbitrary time phase obtained by the contour specifying part as the reference point, and forms the image generation plane including a plane substantially orthogonal to the myocardium at the reference point in the arbitrary time phase;

the image generator generates image data on the image generation plane in the arbitrary time phase based on the volume data acquired in the arbitrary time phase; and the display controller controls the display to display an image based on the image data in the arbitrary time phase.

10. The ultrasonic image processing apparatus according to claim 9, further comprising:

a computing part configured to obtain motion information indicating a motion state of the myocardium in the each time phase, based on the position of each of the points composing the contour of the each time phase, wherein:

the forming part forms the image generation plane for each time phase;

the image generator generates image data on the image generation plane in the each time phase, for each time phase based on the volume data acquired in the each time phase; and the display controller controls the display to display an image based on the image data in the each time phase and further controls the display to display in a state where motion information indicating a motion state on the image generation plane in the each time phase is superimposed on the image for each time phase.

11. A method for processing an ultrasonic image, comprising:

acquiring volume data by driving an ultrasonic probe to transmit ultrasonic waves to a subject;

storing the volume data indicating the subject in a storage;

specifying a 3-dimensional contour of a myocardium based on the stored volume data;

setting a reference point on the contour of the myocardium, and forming an image generation plane including a plane substantially orthogonal to the contour of the myocardium at the reference point;

generating image data on the image generation plane based on the volume data; and displaying an image based on the image data on a display.

12. The method for processing an ultrasonic image according to claim 11, wherein:

a first plane intersecting the contour of the myocardium is set, a point where the first plane intersects the contour of the myocardium is obtained, the point is set as the reference point, and the image generation plane including a second plane substantially orthogonal to the myocardium at the reference point is formed; and image data on the image generation plane including the second plane is generated based on the volume data.

13. The method for processing an ultrasonic image according to claim 12, wherein:

a reference axis piercing the contour of the myocardium is set, a designation of an arbitrary point on the reference axis is received, a point where the first plane passing through the designated point intersects the contour of the myocardium is obtained, the point is set as the reference point, and the image generation plane including the second plane substantially orthogonal to the myocardium at the reference point is generated.

14. The method for processing an ultrasonic image according to claim 13, wherein:

long-axis image data in a cross-section along a long-axis direction of a heart is generated based on the volume data;

a long-axis image based on the long-axis image data is displayed;

the reference axis piercing the long-axis image along the long-axis direction is set, a designation of an arbitrary point on the reference axis is received, a point where the first plane passing through the designated point and substantially orthogonal to the reference axis intersects the contour of the myocardium is obtained, the point is set as the reference point, and the image generation plane including the second plane substantially orthogonal to the myocardium at the reference points is formed;

short-axis image data on the image generation plane including the second plane is generated based on the volume data; and a short-axis image is displayed based on the short-axis image data.

15. The method for processing an ultrasonic image according to claim 12, wherein:

the image generation plane is formed by connecting the first plane with the second plane at the reference point; and image data on the image generation plane formed by connecting the first plane with the second plane is generated based on the volume data.

16. The method for processing an ultrasonic image according to claim 12, wherein:

the image generation plane is formed by extending the second plane to the reference axis; and image data on the image generation plane formed by the second plane extended to the reference axis is generated based on the volume data.

17. The method for processing an ultrasonic image according to claim 12, wherein:

a point where the first plane intersects the specified contour of the endocardium or epicardium of the myocardium is obtained, and the point is set as the reference point.

18. The method for processing an ultrasonic image according to claim 11, wherein:

the volume data acquired for each time phase by transmission of ultrasonic waves to the subject is received, and a position of each of points composing the 3-dimensional contour of the myocardium in the volume data acquired in each time phase is obtained for each time phase by pattern matching;

motion information indicating a motion state of the myocardium in the each time phase is obtained based on the position of each of the points composing the contour in the each time phase;

a reference point is set on the contour of the myocardium in an arbitrary time phase, and the image generation plane is formed for the myocardium in the arbitrary time phase;

image data on the image generation plane in the arbitrary time phase is generated based on the volume data acquired in the arbitrary time phase; and the motion information indicating a motion state on the image generation plane in the arbitrary time phase is displayed in a superimposed state on an image based on the image data in the arbitrary time phase.

19. The method for processing an ultrasonic image according to claim 11, wherein:

the volume data acquired for each time phase by transmission of ultrasonic waves to the subject is received, and a position of each of points composing the 3-dimensional contour of the myocardium in the volume data acquired in each time phase is obtained for each time phase by pattern matching;

a designation of an arbitrary plane intersecting volume data acquired in a specified time phase is received, a point where the arbitrary plane intersects the contour of the myocardium is obtained, a position of the intersecting point in the arbitrary time phase is set as the reference point, and the image generation plane including a plane substantially orthogonal to the myocardium at the reference point in the arbitrary time phase is formed;

image data on the image generation plane in the arbitrary time phase is generated based on the volume data acquired in the arbitrary time phase; and an image based on the image data in the arbitrary time phase is displayed.

20. The method for processing an ultrasonic image according to claim 19, wherein:

motion information indicating a motion state of the myocardium in the each time phase is obtained based on the position of each of the points composing the contour in the each time phase;

the image generation plane is formed for each time phase;

image data on the image generation plane in the each time phase is generated based on the volume data acquired in the each time phase; and an image based on the image data in the each time phase is displayed for each time phase, and further motion information indicating a motion state on the image generation plane in the each time phase is displayed in a superimposed state on the image for each time phase.

* * * * *